United States Patent
Yeung et al.

(10) Patent No.: US 10,842,148 B2
(45) Date of Patent: Nov. 24, 2020

(54) COLLOIDAL ANTIMICROBIAL AND ANTI-BIOFOULING COATINGS FOR SURFACES

(71) Applicant: THE HONG KONG UNIVERSITY OF SCIENCE AND TECHNOLOGY, Hong Kong (CN)

(72) Inventors: King Lun Yeung, Hong Kong (CN); Hanrong Zhang, Hong Kong (CN); Ying Li, Hong Kong (CN); Awais Farid, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 16/310,631

(22) PCT Filed: Jun. 30, 2017

(86) PCT No.: PCT/CN2017/091132
§ 371 (c)(1),
(2) Date: Dec. 17, 2018

(87) PCT Pub. No.: WO2018/001359
PCT Pub. Date: Jan. 4, 2018

(65) Prior Publication Data
US 2019/0174749 A1   Jun. 13, 2019

Related U.S. Application Data

(60) Provisional application No. 62/493,330, filed on Jun. 30, 2016.

(51) Int. Cl.
*A01N 25/28* (2006.01)
*A61L 2/232* (2006.01)
(Continued)

(52) U.S. Cl.
CPC ............. *A01N 25/28* (2013.01); *A01N 25/10* (2013.01); *A01N 25/26* (2013.01); *A01N 31/02* (2013.01);
(Continued)

(58) Field of Classification Search
None
See application file for complete search history.

(56) References Cited

U.S. PATENT DOCUMENTS

2008/0147019 A1* 6/2008 Song ................. C08B 37/003
604/265
2011/0293690 A1* 12/2011 Griffin ................... A61L 27/18
424/443

(Continued)

FOREIGN PATENT DOCUMENTS

WO          01/96012 A1    12/2001
WO    WO-2016041488 A1 *  3/2016   ............. A01N 37/16

OTHER PUBLICATIONS

Extended European Search Report dated Dec. 16, 2019, for corresponding EP application No. 17819356.1.

*Primary Examiner* — Cachet I Proctor
(74) *Attorney, Agent, or Firm* — Nath, Goldberg & Meyer; Joshua B. Goldberg

(57) ABSTRACT

Methods and formulations for antimicrobial and anti-biofouling coating comprising: a hollow round colloidal structure, comprising: an active polymer shell; and an active or inert core; wherein the active polymer shell comprises one and more polymers with antimicrobial and anti-biofouling activities selected from the group consisting of polyethylenimine (PEI), functionalized chitosan (CHI), polyquaternium, poly(diallyldimethylammonium chloride) (PDDA) and polyhexamethylene biguanide (PHMD); wherein the active or inert core contains one and more disinfectants, biocides, fragrances or inert solvent; and wherein the hollow round colloidal structure is stable for at least 3 months.

20 Claims, 39 Drawing Sheets
(18 of 39 Drawing Sheet(s) Filed in Color)

(51) Int. Cl.
| | |
|---|---|
| *C09D 5/14* | (2006.01) |
| *A01N 25/10* | (2006.01) |
| *A01N 35/02* | (2006.01) |
| *A01N 47/44* | (2006.01) |
| *A01N 65/22* | (2009.01) |
| *C09D 5/16* | (2006.01) |
| *D06M 13/13* | (2006.01) |
| *D06M 15/333* | (2006.01) |
| *D06M 15/356* | (2006.01) |
| *D06M 15/53* | (2006.01) |
| *D06M 15/61* | (2006.01) |
| *A01N 49/00* | (2006.01) |
| *A01N 25/26* | (2006.01) |
| *A01N 33/12* | (2006.01) |
| *A01N 33/04* | (2006.01) |
| *D06M 16/00* | (2006.01) |
| *D06M 13/00* | (2006.01) |
| *D06M 15/263* | (2006.01) |
| *D06M 15/03* | (2006.01) |
| *A01N 31/02* | (2006.01) |
| *B01D 67/00* | (2006.01) |
| *B01D 69/02* | (2006.01) |
| *C09D 101/10* | (2006.01) |
| *C09D 105/08* | (2006.01) |
| *C09D 133/14* | (2006.01) |
| *C09D 139/04* | (2006.01) |
| *C09D 139/06* | (2006.01) |
| *C09D 179/02* | (2006.01) |
| *D06M 13/144* | (2006.01) |
| *D06M 23/12* | (2006.01) |

(52) U.S. Cl.
CPC ............ *A01N 33/04* (2013.01); *A01N 33/12* (2013.01); *A01N 35/02* (2013.01); *A01N 47/44* (2013.01); *A01N 49/00* (2013.01); *A01N 65/22* (2013.01); *A61L 2/232* (2013.01); *B01D 67/0093* (2013.01); *B01D 69/02* (2013.01); *C09D 5/14* (2013.01); *C09D 5/1637* (2013.01); *C09D 101/10* (2013.01); *C09D 105/08* (2013.01); *C09D 133/14* (2013.01); *C09D 139/04* (2013.01); *C09D 139/06* (2013.01); *C09D 179/02* (2013.01); *D06M 13/005* (2013.01); *D06M 13/13* (2013.01); *D06M 13/144* (2013.01); *D06M 15/03* (2013.01); *D06M 15/263* (2013.01); *D06M 15/333* (2013.01); *D06M 15/3562* (2013.01); *D06M 15/53* (2013.01); *D06M 15/61* (2013.01); *D06M 16/00* (2013.01); *D06M 23/12* (2013.01); *B01D 2325/48* (2013.01)

(56) References Cited

U.S. PATENT DOCUMENTS

| | | | |
|---|---|---|---|
| 2012/0021034 A1* | 1/2012 | Zink | A01N 59/16 424/421 |
| 2013/0220331 A1* | 8/2013 | Yahiaoui | A61M 16/04 128/207.14 |
| 2015/0210965 A1* | 7/2015 | Bertram | A01N 25/28 424/401 |

* cited by examiner

|  | Control | Treated samples | Bactericidal efficiency |
|---|---|---|---|
| Top | 46 | 0 | 100% |
| Center | 56 | 0 | 100% |
| Bottom | 52 | 2 | 96.15% |
| Overall reduction | 98.70% | | |

COLLOIDAL ANTIMICROBIAL AND ANTI-BIOFOULING COATINGS FOR SURFACES

CROSS-REFERENCE TO RELATED APPLICATION

This is a National Phase Application filed under 35 U.S.C. 371 as a national stage of PCT/CN2017/091132, filed Jun. 30, 2017, an application claiming priority to U.S. Provisional Application No. 62/493,330 filed Jun. 30, 2016, the content of which is hereby incorporated by reference in its entirety.

BACKGROUND

The present subject matter relates to the technical field of surface coatings for solid and porous surfaces, and specifically to coating materials possessing a combination of antimicrobial, contact-killing and anti-adhesion properties. The details of the methods of preparation, as well as the properties and performances of the coating, are also disclosed.

Globally, according to the World Health Organization, waterborne disease and water related disease are leading killers resulting in more than 3.4 million deaths annually. Water sources and surfaces exposed to water are susceptible to contamination and fouling, even in closed systems, from the development of biofilms which act as key reservoirs for microbial contaminations. Water filtration membranes employed for water purification and to safeguard drinking water from contaminants are easily affected, because microbes present in the water can colonize the membrane resulting in biofouling. Biofouling can lead to a serious and significant loss in performance and a shortening of operational lifetime of the membrane, and contaminated membranes can become reservoirs for opportunistic pathogens. As a result, filtration membranes designed with anti-fouling properties have been widely investigated.

U.S. Published Patent Application No. 2010/0133172 describes a complex, hydrophilic-like composition made mainly of hydrophilic polymer, polyphenolic compound and surfactant coated on perm-selective membrane designed to resist fouling from waterborne contaminants. U.S. Pat. No. 4,634,530 describes a process for chemically modifying a preformed polybenzimidazole semipermeable membrane based on sulfonating the membrane resulting in an increased resistance to fouling. U.S. Pat. No. 6,177,011 describes a reverse osmosis composite membrane with a high fouling tolerance provided by coating aromatic polyamide with polyvinyl alcohol. U.S. Pat. No. 6,280,853 describes a composite membrane with a porous support and a cross-linked polyamide surface having polyalkylene oxide groups grafted thereto exhibiting improved resistance to fouling. U.S. Published Patent Application No. 2012/0048799 describes a composite membrane with a cross-linkable polymer comprising a poly(meth)acrylate and/or poly(meth)acrylamide backbone and a multi-functional acid halide crosslinking agent with anti-fouling properties. U.S. Published Patent Application No. 2013/0240445 describes a filtration membrane coated with a polymer comprising a benzenediol or a substituted phenol with anti-fouling properties requiring repetitive cleaning and reapplication for long-term use. U.S. Published Patent Application No. 2012/0211414 describes a selective membrane with high fouling resistance using hydrophilic coatings on reverse-osmosis membranes.

Other surfaces at risk for biofouling and microbial growth include municipal drinking water distribution pipe networks and holding tanks. Sewers and drainage systems, heat exchangers and cooling towers also provide environments favorable to the formation of biofilms. A 2 mm thick microbial surface layer is estimated to result in 80% energy loss in cooling tower systems. Accordingly, protective coatings for these solid surfaces have been developed.

CN 101143994B describes an antifouling paint composed mainly of copper and zinc ions. U.S. Published Patent Application No. 2012/0135149 describes an anti-biofouling coating for use in contact with water composed of a macromolecular scaffold containing reactive groups capable of undergoing a Michael-type reaction. U.S. Pat. No. 8,080,285 B2 describes an anti-biofouling coating containing a polysiloxane-based polymer and cylindrical nanofiller released particles into the water. U.S. Published Patent Application No. 2014/0148552 A1 describes a biomimetic agent for anti-biofouling composed of an anchoring moiety allowing for surface attachment and a zwitterionic moiety exhibiting anti-biofouling activity.

Currently, there remains a need in the art for antimicrobial and anti-biofouling coatings with long term activities which are capable of application to both solid and nonsolid surfaces. The present subject matter is directed to colloidal antimicrobial and anti-biofouling coatings for both reversible and irreversible coating on solid and porous surfaces affording wide-spectrum antimicrobial properties, arresting microbial biofilm formation and preventing biofouling. The present coating is designed for a variety of applications, and especially ideal for coating water filtration membranes, pipes, tubing and other surfaces in contact with water, as well as textiles and other porous media including air particulate filters. The present compositions are also effective as antimicrobial and anti-biofouling coatings for solid and porous surfaces exposed to air. The colloidal antimicrobial and anti-biofouling coatings are capable of storing and releasing disinfectants, biocides and fragrances.

BRIEF SUMMARY

The present subject matter relates to an antimicrobial and anti-biofouling coating formulation, comprising:
  a hollow round colloidal structure, comprising:
    a) an active polymer shell; and
    b) an active or inert core;
  wherein the active polymer shell comprises one and more polymers with antimicrobial and anti-biofouling activities selected from the group consisting of polyethylenimine (PEI), functionalized chitosan (CHI), polyquaternium, poly(diallyldimethylammonium chloride) (PDDA) and polyhexamethylene biguanide (PHMD);
  wherein the core is active and contains one or more disinfectants, biocides and fragrances; and
  wherein the core is inert and contains water or inert solvent; and
  wherein the hollow round colloidal structure is stable for at least 3 months.

In another aspect, the present subject matter relates to a method of producing antimicrobial and anti-biofouling coating for application to nonporous surfaces, porous membranes or porous materials, comprising:
  preparing an antimicrobial and anti-fouling formulation by the steps of:
    (a) preparing an aqueous solution containing one or more active polymers;

(b) adding biocides or solvents into the aqueous solution of active polymers;

(c) preparing an emulsion having a hollow round colloidal structure comprising adding a stabilizer mixture containing one and more surfactants to the biocides or solvents and solution of active polymers to form the antimicrobial and anti-biofouling formulation; and (d) preparing the antimicrobial and anti-biofouling coating from the antimicrobial and anti-biofouling formulation; and applying the antimicrobial and anti-biofouling coating on nonporous surfaces, porous membranes or porous materials.

The compositions and methods of the present subject matter address the problems and issues of the prior art compositions and methods, as provided in more detail accordingly.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
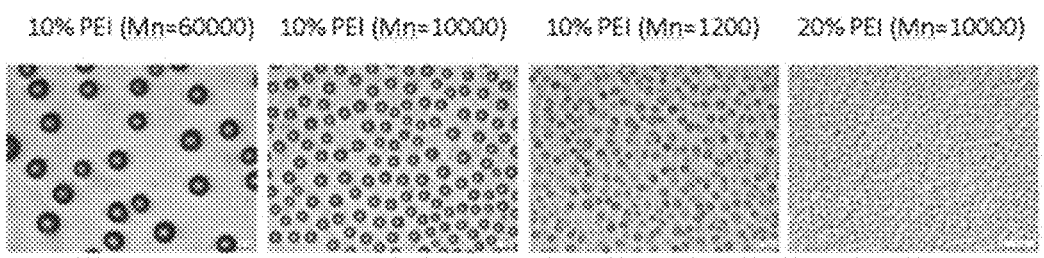
FIG. 1: Optical microscopy images of colloids formed by PEI with molecular weight from 1300 to 60000 and polyvinyl alcohol (PVA).
Figure 2:
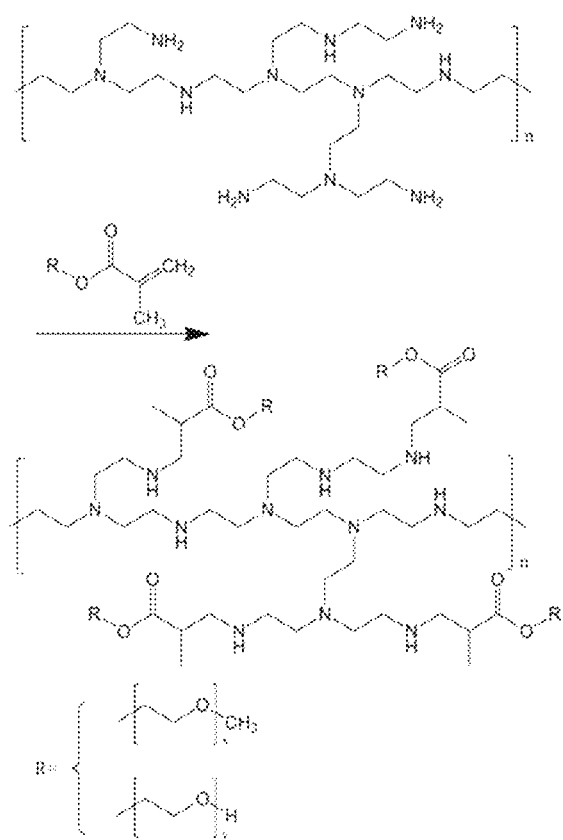
FIG. 2: Chemical crosslinking of PEI polymers in the colloidal antimicrobial and anti-biofouling coating material.

The present chemical compositions are colloidal antimicrobial and anti-biofouling coatings, having ideal physical characteristics for application to solid and porous surfaces exposed to air and water/liquid environments. Biofouling or biological fouling is generally defined as the accumulation of microorganisms, plants, algae, or animals on wetted surfaces.

The present coating is a colloidal suspension of hollow, round particles comprising at least two or more polymers such as functionalized biopolymers (chitosan), phosphatidylcholine as well as polymer chains containing primary, secondary and/or tertiary amines and zwitterionic groups. The preparation of the coating compositions is such that the polymers self-assembled into hollow round particles at a given concentration and pH. The particle size can be controlled with the use of a stabilizer and/or also through cross-linking. The hollow, round particles can contain cores of either inert or active ingredients. An inert (non-antimicrobial) core may contain, for example, water or an inert solvent. An active (antimicrobial) core may contain, for example, one or more disinfectants, biocides-and fragrances.

The stabilizer can be selected from polyvinyl alcohol (PVA) and/or polyethylene glycol (PEG) derivatives, as well as polymers with PVA or PEG groups can be applied. In a particular embodiment, the stabilizers are presents as about 0.01-20% (w/v) of PVA mw 31,000-186,000 g/mol; about 0.01-20% (w/v) of PEGMA Mn=200-1000, preferably 500; and about 0.01-20% (w/v) of MPEGMA Mn=200-5000, preferably 950.

The coating of surfaces can be accomplished by spray-coating, dip-coating, wash-coating and wiping, or via use of chemical linkers. Complex coatings can be assembled using a layer-by-layer coating method. Furthermore, paint and epoxy resin coatings containing the instant colloids can directly applied on surfaces. In all case, the instant coatings are stable in air and water, and resist erosion by water flow. The coating is designed to be safe and effective for industrial, commercial, municipal and household usage.

Colloidal antimicrobial and anti-biofouling coatings comprise polymers include, but are not limited to, active polymers such as polyethylenimine (PEI), poly(diallyldimethylammonium chloride) (PDDA), polyhexamethylene biguanide (PHMD), chitosan (CHIT), polyquaternium (PQAC), and polyvinyl alcohol (PVA). It is contemplated that specific active polymers are defined as those having low adhesion properties and/or beneficial antimicrobial properties.

Chemical cross-linking can attach L-α-phosphatidylcholine (EGG), 2-(diethylamino)ethylmethacrylate (NR3), [3-(methacryloylamino)propyl)dimethyl-(3-sulfopropyl)ammonium hydroxide (NR4) and 3-sulfopropyl methacrylate (SO3) onto the main polymer materials. Detailed methods of preparation are described in Examples 1-12 as described after discussion regarding the Figures.

Discussion of Figures

The following discussion of the Figures references the Examples as described in the following section. Reference is made to specific Examples. It is to be noted that all Figures and Examples are not meant to be limiting to the subject matter claimed in the appended claims.

Figure 3:
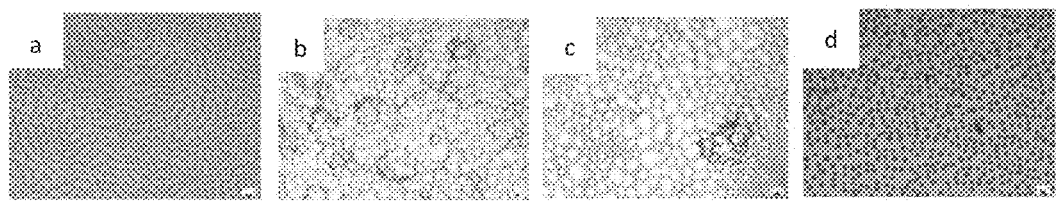
FIG. 3: Optical microscopy images of colloids formed by PEI-PHMB with ratios of (a) 4:1, (b) 2:1, (c) 1:2 and (d) 1:4.
Figure 15:
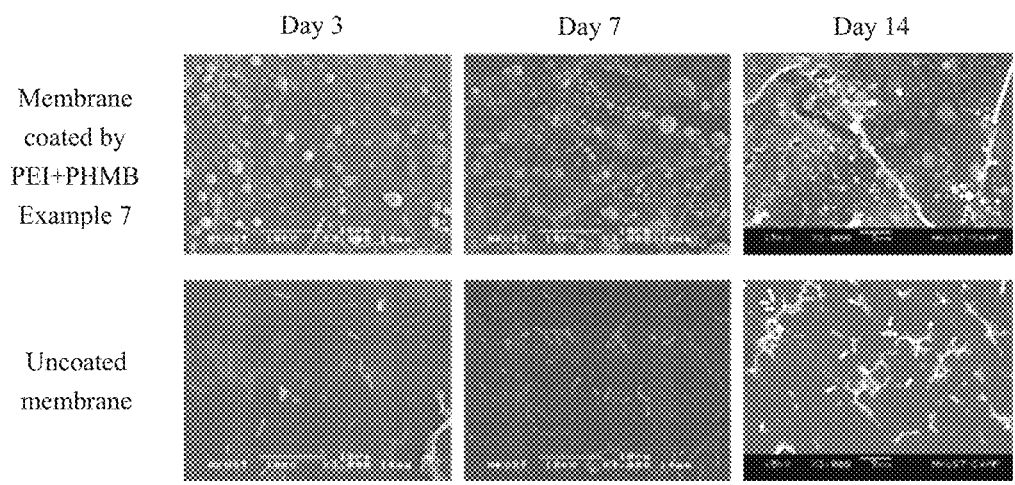
FIG. 15: Anti-biofouling performance as indicated by microbial attachment on the nanofiltration membrane for uncoated and PEI-PHMB (Example 8) coating. Test organism: $10^6$ CFU/ml E. coli.
Figure 16:
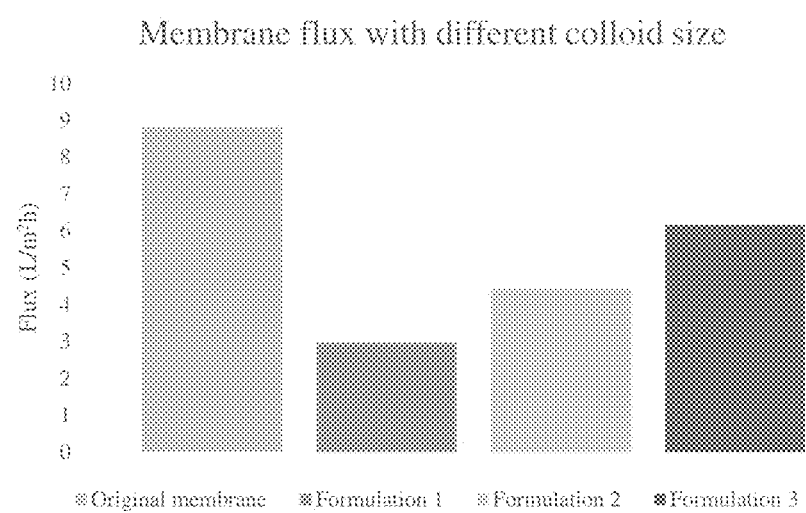
FIG. 16: Water flux across the nanofiltration membrane.
Figure 17:
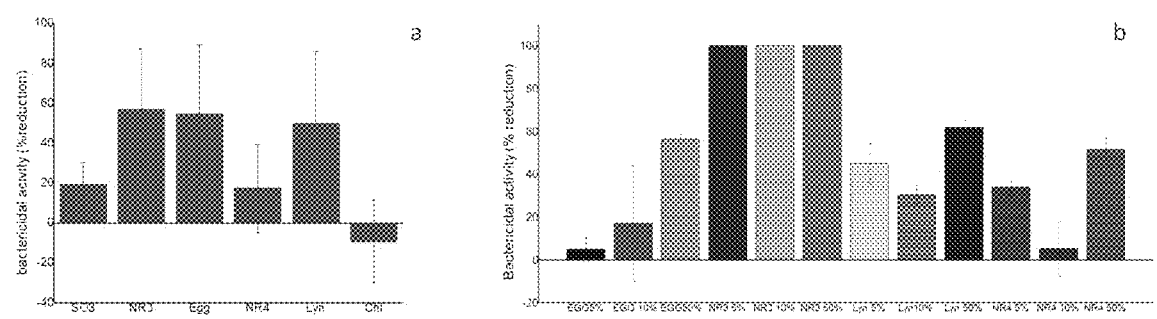
FIG. 17: (a) Bactericidal activities of colloidal PEGDA-X (where X is CHIT, EGG, NR3, NR4, SO3 and LYN) (Example 4), (b) bactericidal activities of different amounts of PEGDA-EGG, PEGDA-NR3, PEGDA-LYN and PEGDA-NR4.
Figure 18:
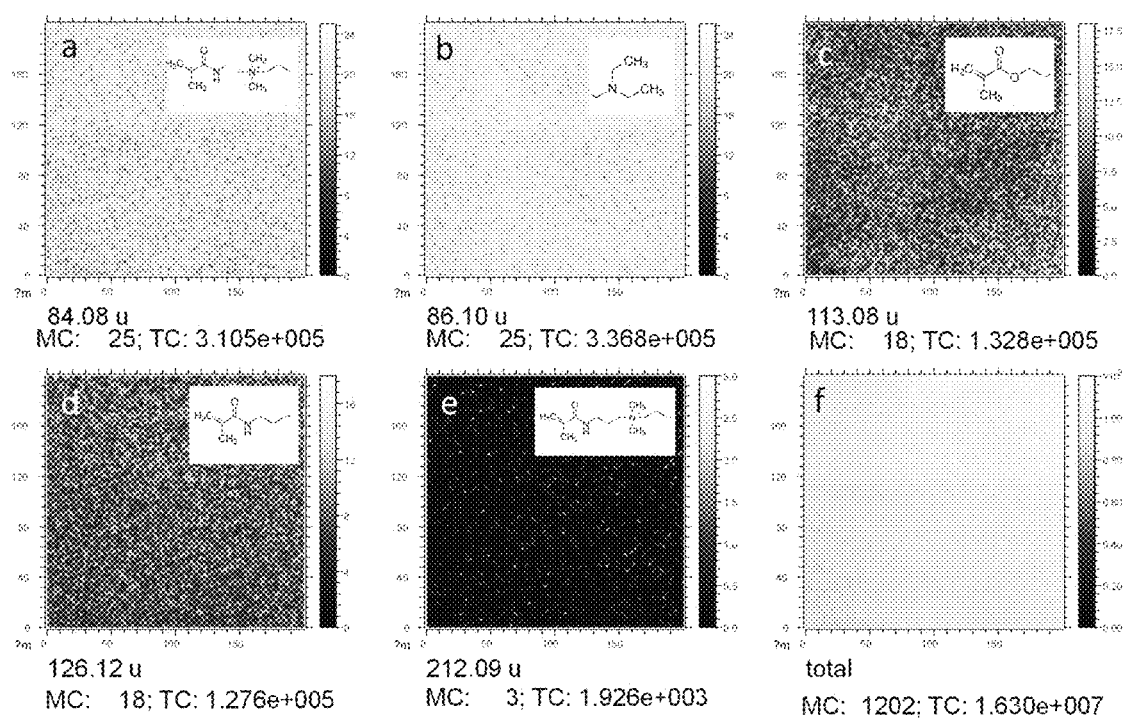
FIG. 18: Time-of-flight secondary ion mass spectroscopy (ToF-SIMS) images of coated nanofiltration membranes. Fragments located at m/z of 86 and 113 belong to NR3, while those at m/z of 84, 126, and 213 belong to NR4.

The colloids of the instant coatings can range in size to accommodate different coating functions. For example, increasing colloid size can increase water flux when the coatings are used in a filtering application as shown in FIG. 16. Various factors influence the size of the colloid particles. For example, the size of the colloidal particles can be controlled by adjusting the molecular weight of the constituent polymers. FIG. 1 shows a series of optical microscopy images of PEI colloidal antimicrobial and anti-biofouling coating formulations: 10% PEI (Mn 60,000), 10% PEI (Mn 10,000) and 10% PEI (Mn 1,200). PEI with lower molecular weight (ca. 1,200 g/mol) formed 2 micron colloids, whereas PEI with higher molecular weight (ca. 60,000 g/mol) formed 20 micron colloids. Increasing the amount of constituent polymer, in FIGS. 1 to 20% PEI (mw 10,000), also modifies the size of the colloidal particles. In the case of polymers, molecular weight (mw) means average molecular weight. Varying the compositional ratios of active polymers also varies the particle size. From left to right, the particle sizes were 2 μm, 1 μm, 0.8 μm and 0.5 μm. In FIG. 3, the colloidal PEI-PHMB antimicrobial and anti-biofouling coating, was prepared with different compositional ratios of PEI and PHMB ((a) 4:1, (b) 2:1, (c) 1:2 and (d) 1:4), thereby varying the colloidal particle size from 5-20 microns. Specifically, in FIG. 3, the particle sizes achieved were (a) 1 μm, (b) 0.5-2 μm, (c) 2-3 μm and (d) 0.5 μm.

The particle size can be controlled with cross-linking, which increases the polymer length and grafts different functional moieties or polymers to create new properties and functions. This approach can be used to incorporate zwitterionic molecules, metal biocides and biocidal proteins and enzymes to the primary polymer. For example, PEI can be cross-linked according to the general reaction shown in FIG. 2.

Colloidal particle size can also be controlled with the use of stabilizer and is also influenced to a lesser extent by the pH and concentration. Table 1 shows colloidal antimicrobial and anti-biofouling coating comprising of different concentrations of PEI and PHMB.

TABLE 1

| Sample No. | PHMB (20%) (µl) | PEI (20%) (µl) | DDI (µl) | PEI:PHMB |
|---|---|---|---|---|
| 1 | 50 | 50 | 0 | 1:1 |
| 2 | 50 | 25 | 25 | 2:1 |
| 3 | 50 | 12.5 | 37.5 | 4:1 |
| 4 | 25 | 50 | 25 | 1:2 |
| 5 | 12.5 | 50 | 37.5 | 1:4 |
| C1 | 50 | 0 | 50 | N/A |
| C2 | 0 | 50 | 50 | N/A |

Figure 4:
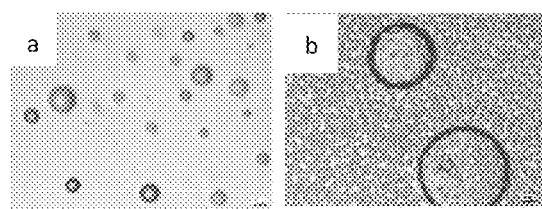
FIG. 4: Optical microscopy images of colloids formed from (a) PHMB and (b) PEI storing thyme oil.
Figure 5:
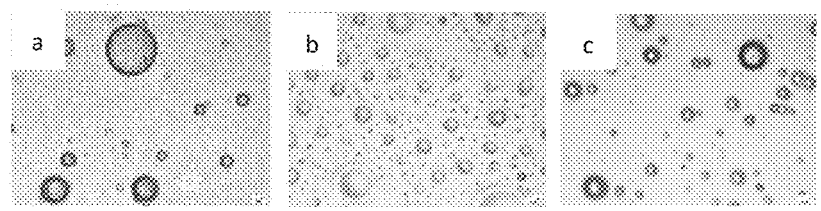
FIG. 5: Optical microscopy images of colloids formed from PEI-PHMB storing thyme oil. PEI-PHMB with different ratios of (a) 4:1, (b) 1:1 and (c) 1:4.
Figure 6:
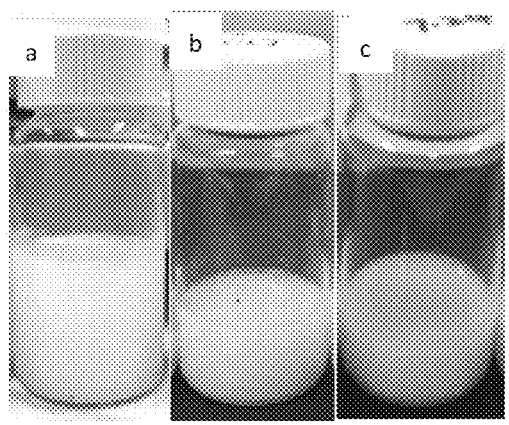
FIG. 6: Photos of the emulsions of PEI colloids storing (a) cinnamaldehyde, (b) farnesol and (c) mixed biocides.

The colloid particle size may further be varied to accommodate an active core material. Microscopy images (FIGS. 1 and 3-5) confirm that the instant colloidal particles of the antimicrobial and anti-biofouling coating are round and hollow, and thereby capable of containing an active core material. An active core material can be, for example, essential oils, fragrances, biocides and/or disinfectants. Biocides include with polyols, such as farnesol, cinnamaldehyde, and thyme oil, as well as mixed biocides (thyme oil, cinnamaldehyde and farnesol). Some active cores may be essential oils, which are active as fragrances, disinfectants and biocides. Methods of preparing colloidal particles containing, storing and releasing essential oil, fragrance, biocide and disinfectant in formulated coatings are found in Examples 13-22. FIGS. 4 and 5 show the colloidal antimicrobial and anti-biofouling coating formulation containing thyme oil. PEI, PHMB and PEI-PHMB colloids and thyme oil were successfully formulated (Examples 13-15). The particle sizes, in FIG. 4, were (a) 2-5 µm and (b) 1 µm. In FIG. 5, the particle sizes were (a) 0.5-2 µm, (b) 1-2 µm and (c) 1-3 µm. When active cores are employed, the instant coating can be a stable colloid suspension form (FIG. 6) for PEI with cinnamaldehyde, farnesol and mixed biocides (thyme oil, cinnamaldehyde and farnesol) as non-limiting examples. Other active core combinations possible according to the instant subject matter utilize the hollow region of the colloidal particles for containing, encapsulating, storing and releasing active materials that include ions, molecules and biomolecules for the purpose of disinfection and inhibition of microbial contaminations.

An example coating formulation comprises, by weight:
a. From about 0.01-20% (w/v) of PVA mw 31,000-186,000 g/mol;
b. From about 0.01-20% (w/v) of PEGMA Mn=500;
c. From about 0.01-20% (w/v) of MPEGMA Mn=950;
d. From 0.0001-5% (w/v) Polyethylenimine mw 1,200-60,000 g/mol; purchased from Sigma Aldrich;
e. From 0.05-3% (w/v) Polyhexamethylene biguanide mw 2,000-2,600 g/mol;
f. From 0.01-20% (w/v) of Poly(diallyldimethylammonium chloride) mw 250,000-350,000 g/mol;
g. From 0.01-1.5% (w/v) of Thyme oil;
h. From 0.01-1.5% (w/v) of Farnesol mw=222 g/mol; and
i. From 0.05-1.5% (w/v) of Cinnamaldehyde mw=132 g/mol.

Accordingly, a particular range of total active polymer is 0.0001-30% (w/v). Ideally, the active polymers are present at 10-20 w % in a ratio of 1-4:4-1.

Figure 7:
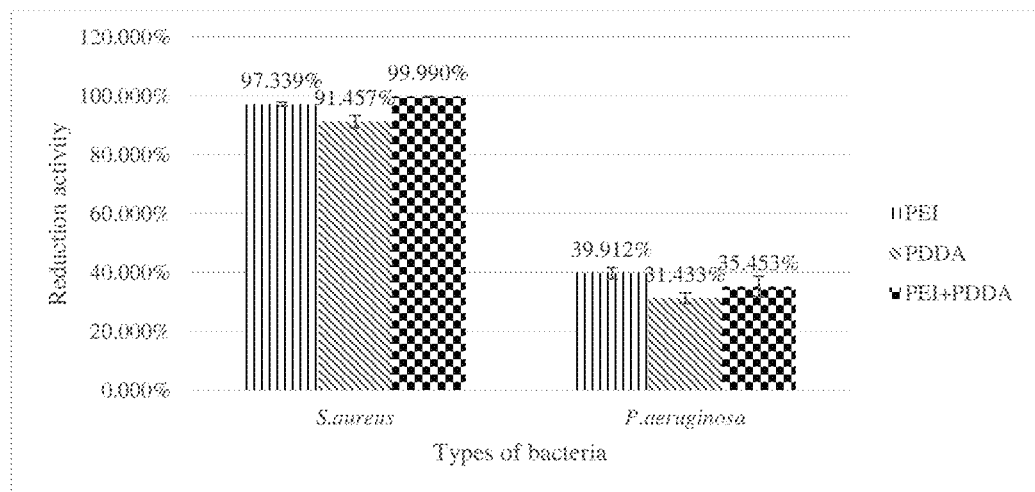
FIG. 7: Antimicrobial performance of PEI (Example 1), PDDA and PEI-PDDA (Example 5) coatings on $10^6$ CFU/ml S. aureus and P aeruginosa.
Figure 8:
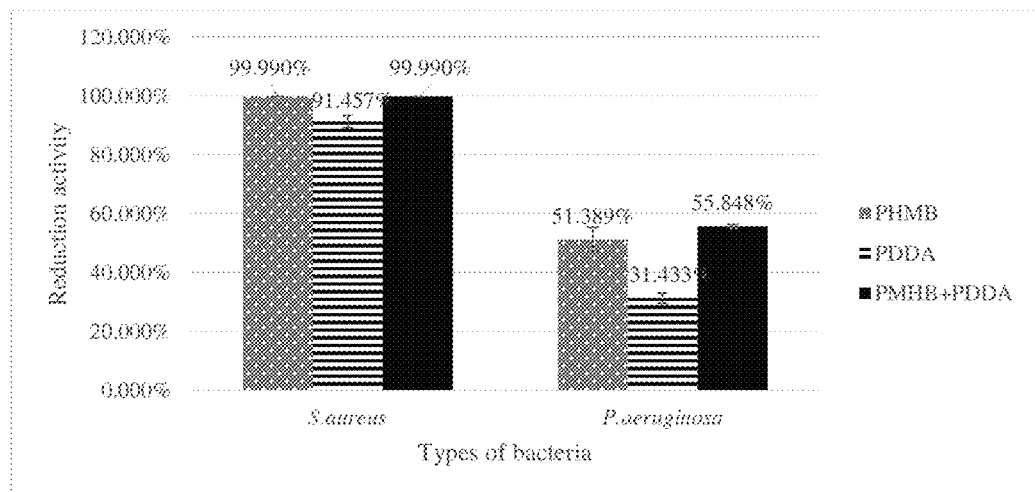
FIG. 8: Antimicrobial performance of PHMB, PDDA and PHMB-PDDA (Example 6) coatings on $10^6$ CFU/ml S. aureus and P aeruginosa.
Figure 9:
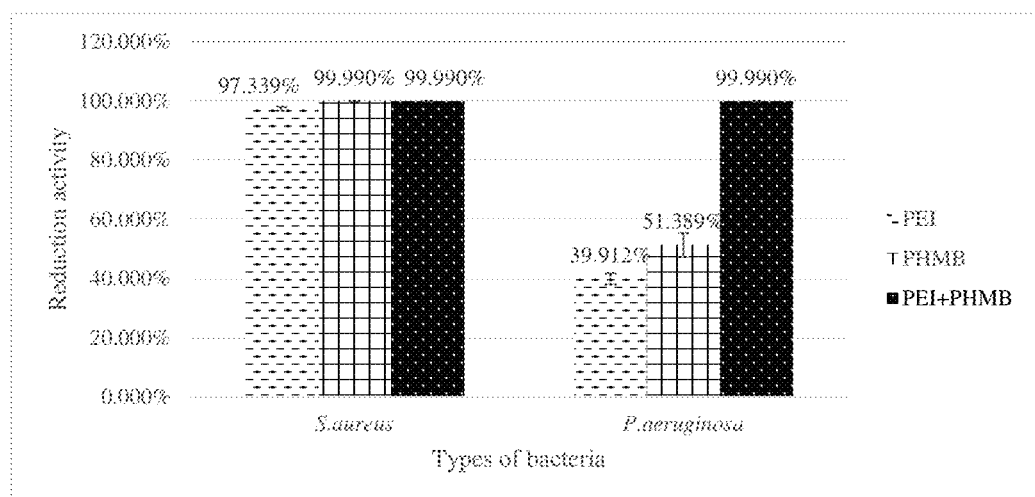
FIG. 9: Antimicrobial performance of PEI, PHMB and PEI-PHMB (Example 7) coatings on $10^6$ CFU/ml S. aureus and P aeruginosa.
Figure 10:
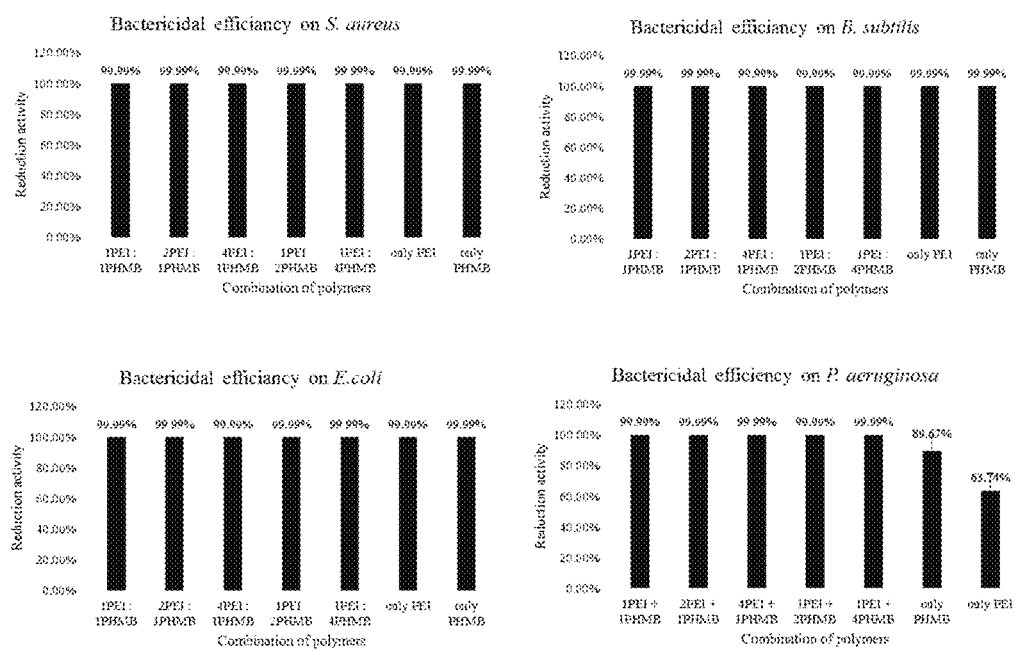
FIG. 10: Antimicrobial performance of PEI, PHMB and PEI-PHMB (Examples 7-12) coatings on $10^6$ CFU/ml S. aureus, B. subtilis, E. coli and P aeruginosa.

FIG. 7 shows the bactericidal properties of PEI (Example 1), PDDA and PEI-PDDA (Example 5) for *S. aureus* and *P. aeruginosa*. A 99.99% (4 Log) reduction in viable *S. aureus* was obtained from the PEI-PDDA coating (97.339% for PEI and 91.457% for PDDA), and a modest 40% reduction for the *P. aeruginosa*. FIG. 8 describes similar bactericidal test on PHMB, PDDA and PHMB-PDDA (Example 6) for *S. aureus* and *P aeruginosa*. A 99.99% (4 Log) reduction in viable *S. aureus* was obtained from PHMB-PDDA coating (99.990% for PHMB and 91.457% for PDDA), and a modest 55% reduction for the *P aeruginosa* (51.389% for PHMB and 31.433% for PDDA). FIG. 9 shows the results for PEI, PHMB and PEI-PHMB (Example 7) for *S. aureus* and *P aeruginosa*. A 99.99% (4 Log) reduction in viable *S. aureus* was obtained from PEI-PHMB coating (97.339% for PEI and 99.990% for PHMB), and a similar 99.99% (4 Log) reduction in the *P aeruginosa* biofilm-forming (39.912% for PEI and 51.389% for PHMB). In the latter case, a synergistic effect of the combination of PEI-PHMB is shown. FIG. 10 plots the bactericidal activities of PEI, PHMB, PEI-PHMB coatings (Examples 7-12) for *S. aureus, B. subtilis, E. coli* and *P aeruginosa*. PEI-PHMB coatings maintained 99.99% (4 Log) reduction in viable bacteria.

Figure 11:
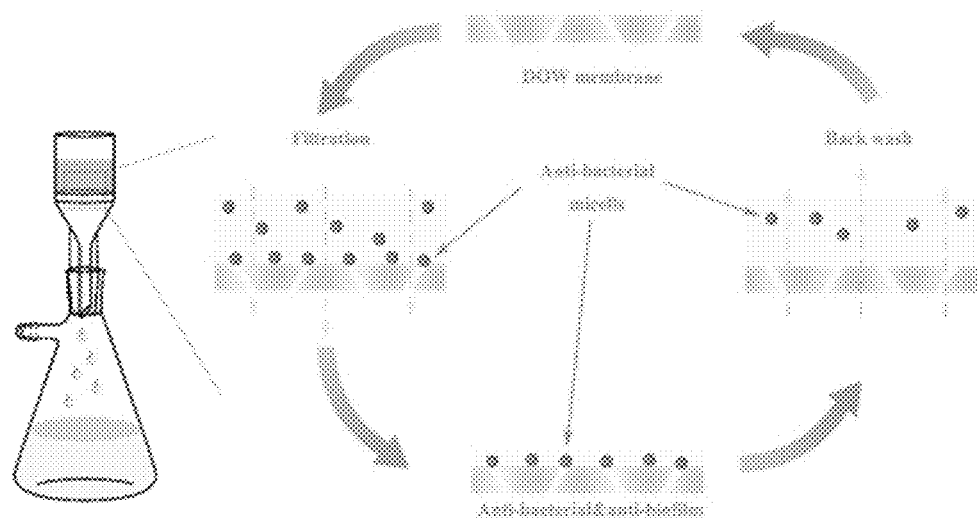
FIG. 11: A schematic illustration of coating process on a water filtration membrane (Examples 23-27). The drawing is for a nanofiltration membrane at laboratory scale.

FIG. 11 illustrates one approach for coating water filtration membranes, such as reverse osmosis (Example 24), nanofiltration (Example 25), ultrafiltration (Example 26) and microfiltration membranes (Example 27) with the instant colloidal antimicrobial and anti-biofouling coating. The method comprises introducing the coating to the membrane through the retentate stream, depositing the colloidal particles via filtration onto the membrane surface and subsequently attached. This method imparts antimicrobial and anti-biofouling properties to the coated membrane. An advantage of this method is that the coating can be simply carried out even in operating membrane system without interruption. The coating can be dislodged by acidic backwashing. Table 2 shows the retention of colloidal antimicrobial and anti-biofouling coating on nanofiltration membranes.

TABLE 2

| Running duration at 3 bar (hour) | Washed-off micelle (µl) | Remaining micelle (µl) | Remaining coating % |
|---|---|---|---|
| 1 | 81 | 919 | 92% |
| 3 | 150 | 850 | 85% |

Figure 12:
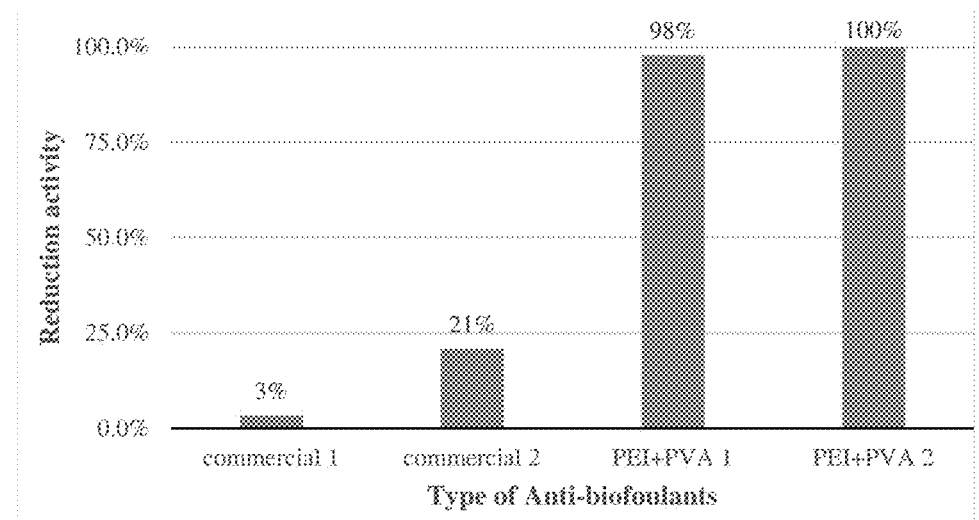
FIG. 12: Antimicrobial performance of 2 commercial tin-based anti-biofoulant and 2 PEI coatings on nanofiltration membrane. Test organism: $10^6$ CFU/ml E. coli.
Figure 13:
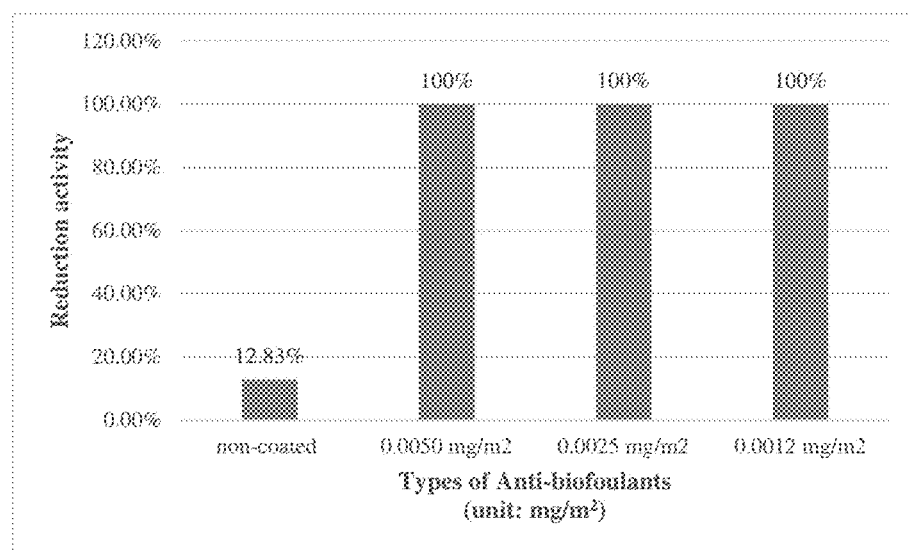
FIG. 13: Antimicrobial performance of different amount of PEI-PHMB (Example 7) surface coating on nanofiltration membrane. Test organism: $10^6$ CFU/ml E. coli.
Figure 14:
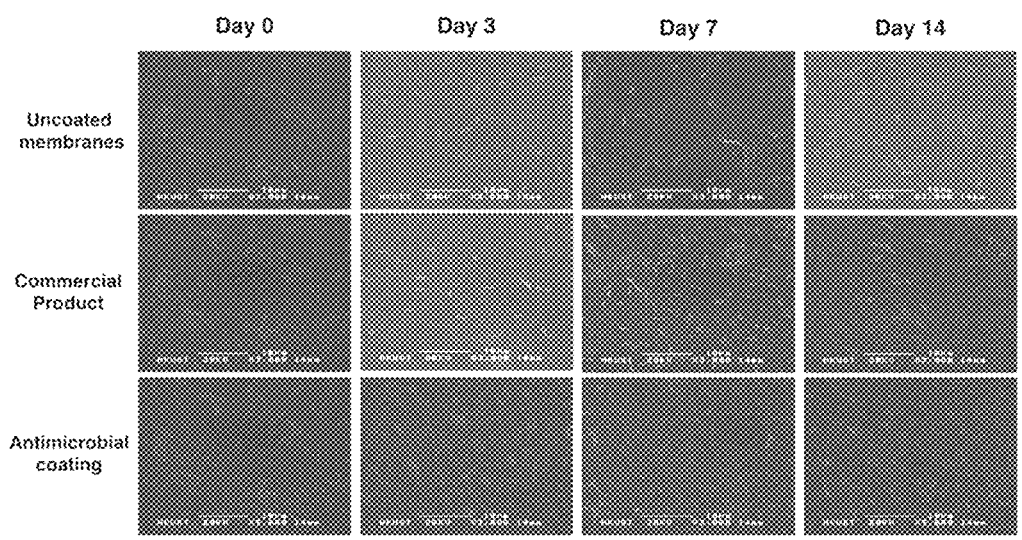
FIG. 14: Anti-biofouling performance as indicated by microbial attachment on the nanofiltration membrane for uncoated, commercial anti-biofoulant and PEI coating (Example 1). Test organism: $10^6$ CFU/ml E. coli.

FIG. 12 compares the antimicrobial properties of two commercial tin-based anti-biofoulants (2,2-dibromo-3-nitrilopropionamide (DBNPA) aqueous solutions with different concentrations, Dow) and two PEI coatings (Example 1) on a nanofiltration membrane. Membranes treated with the commercial anti-biofoulants had low bactericidal properties (3% and 21% reduction in activity), whereas the instant colloidal PEI coatings can achieve better than 97% reduction in viable bacteria. FIG. 13 shows the instant colloidal PEI-PHMB coating (Examples 7 and 27) can maintain better than 99.99% reduction in bacteria compared to uncoated nanofiltration membrane even at very low coating amount. FIG. 14 includes a series of SEM images taken over 14-day period of membrane samples immersed in bacterial culture. The microbial attachment on the nanofiltration membrane coated with the instant colloidal PEI (Example 1) is negligible compared to uncoated membrane and membrane treated with commercial anti-biofoulant (DBPNA, Dow). These studies confirmed that the colloidal coating is both antimicrobial and anti-biofouling. FIG. 15 follows the biofilm growth on nanofiltration membrane for both uncoated and PEI-PHMB coated samples (Examples 8 and 25) at estimated E. coli concentrations of 2500 CFU/cm² and 0 for uncoated and coated samples. The coated membrane was free of E. coli bacteria. FIG. 16 shows the effects of the colloidal PEI-PHMB coatings on water flux. A 99.99% reduction in viable E. coli was maintained in all three formulations, but the size of the colloid particles was increased from 1 to 2 and 10 microns. Using larger colloids with the same amount of coating can ameliorate the effect of coating on water flux. Table 3 shows that the membrane rejection/retention rate was improved with the coating. Rejection data of uncoated and coated membranes shown in Table 3 was produced using methyl orange solution.

TABLE 3

|  | Original Membrane | Coated membrane |
|---|---|---|
| Output Concentration (g/L) | 0.015 | 0.008 |
| Rejection ratio | 70% | 84% |

FIG. 17(a) plots the bactericidal properties of colloidal PEGDA crosslinked with unmodified chitosan (CHIT), L-α-phosphatidylcholine (EGG), 2-(diethylamino)ethylmethacrylate (NR3), [3-(methacryloylamino)propyl]dimethyl-(3-sulfopropyl)ammonium hydroxide (NR4), 3-sulfopropyl methacrylate (SO3), and lysozyme (LYN) (Example 4). PEGDA served as an inert polymer in these samples to which different antimicrobial, anti-adhesion and anti-biofouling molecules could be crosslinked to. FIG. 17b shows the results of further bactericidal studies on EGG, NR3, NR4, and LYN at different compositions. NR3 performed best compared to EGG and LYN. NR4 had lower bactericidal activity, but exhibited excellent anti-adhesion properties. Uniform surface coating can be achieved by simply brush coating the colloidal antimicrobial and anti-biofouling coating (Example 28) as indicated by the ToF-SIMS mapping images of the nanofiltration membrane surface in FIG. 18.

Figure 19:
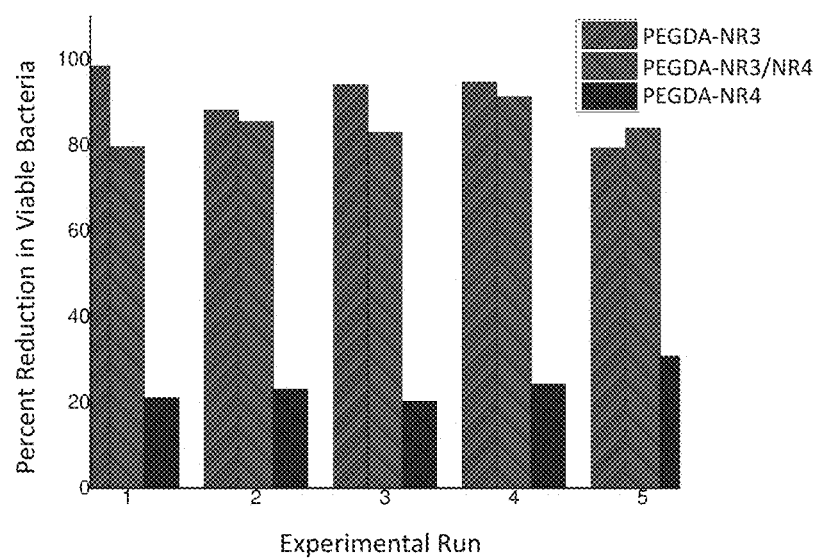
FIG. 19: Plots of the percentage reduction in viable bacteria upon contact with nanofiltration membranes coated with PEGDA-NR3, PEGDA-NR4 and PEGDA-NR3/NR4. Test organism: $10^6$ CFU/ml E. coli.
Figure 20:
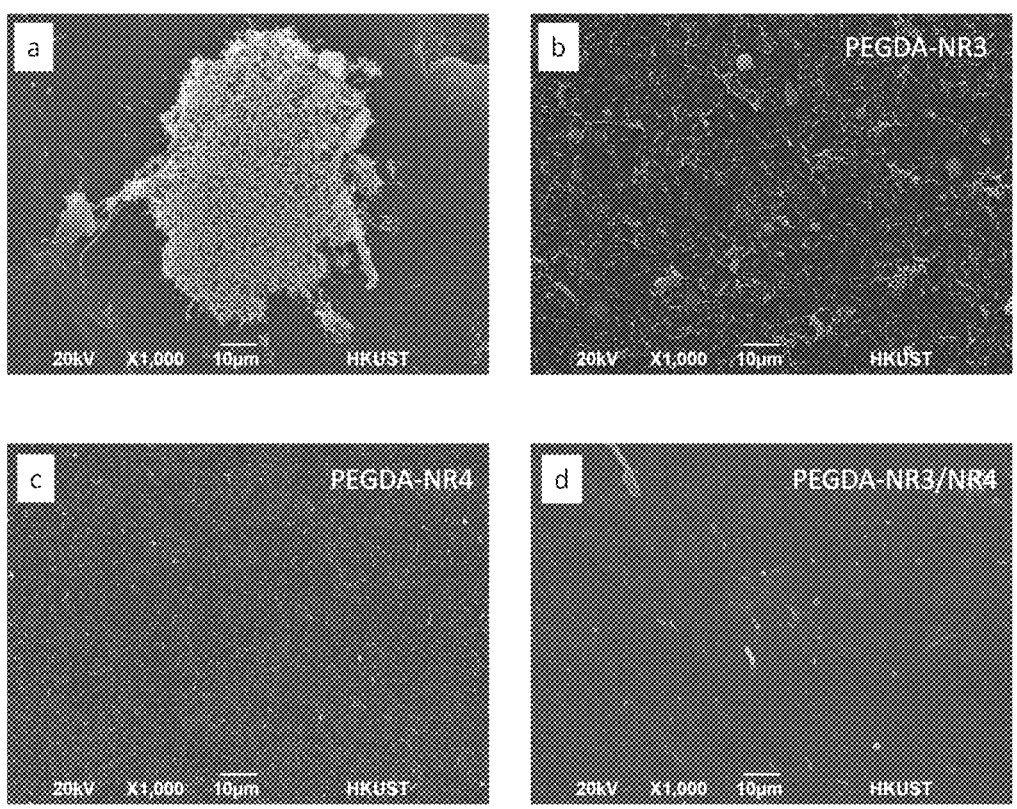
FIG. 20: SEM images of (a) uncoated nanofiltration membrane and nanofiltration membranes coated with (b) PEGDA-NR3, (c) PEGDA-NR4 and (d) PEGDA-NR3/NR4 after 48 h exposure to $10^9$ CFU/ml E. coli.
Figure 21:
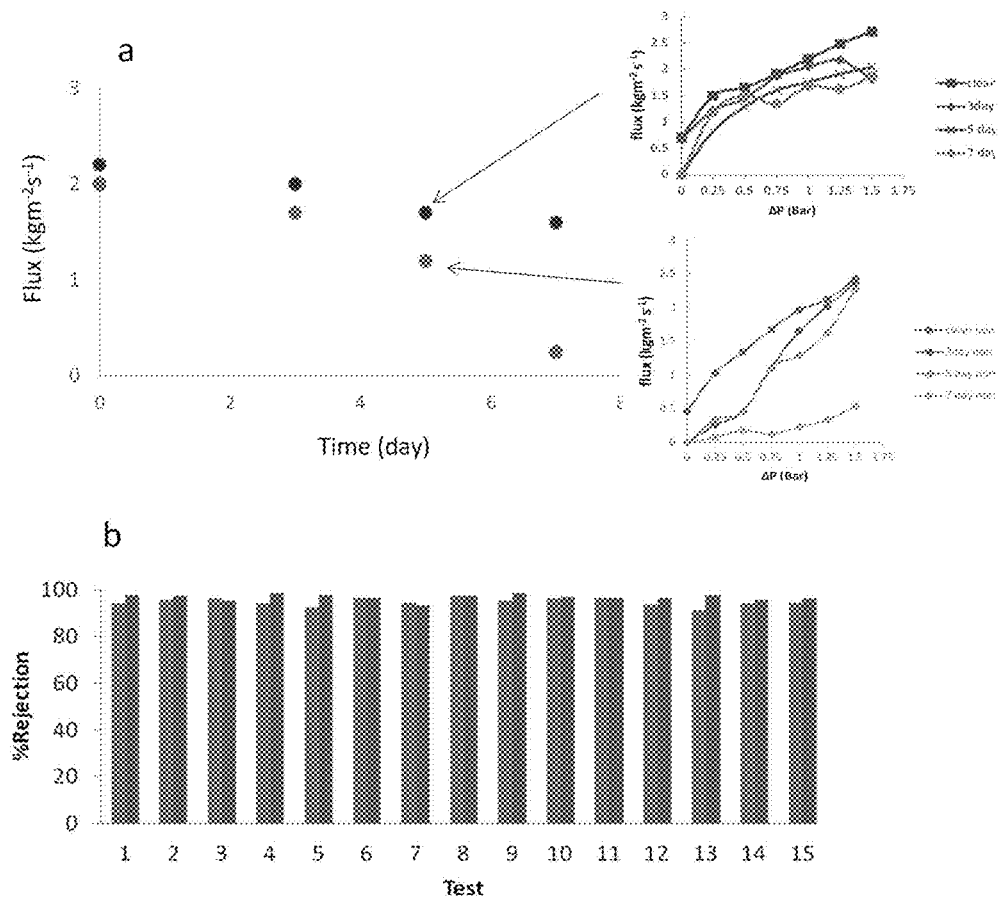
FIG. 21: (a) Water flux through uncoated nanofiltration membrane and nanofitration membrane coated with PEGDA-NR3/NR4 over 7 days using raw water from a surface pond located at the university. (b) Results of dye rejection experiment on uncoated nanofiltration membrane and nanofitration membrane coated with PEGDA-NR3/NR4 over the 7 days experiment.
Figure 22:
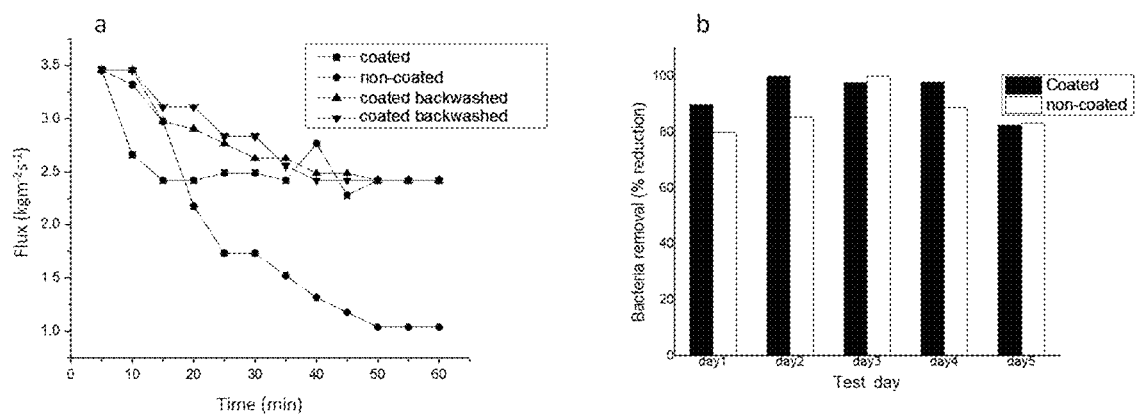
FIG. 22: (a) Water flux through uncoated microfiltration membrane and microfitration membrane coated with PEGDA-NR3/NR4 at 0.1 L/min, and (b) bacterial removal rate of the membranes.

FIGS. 19 and 20 plot the antimicrobial and anti-biofouling results for an uncoated nanofiltration membrane, and nanofiltration membranes coated with colloidal PEGDA-NR3, PEGDA-NR4 and the PEGDA-NR3/NR4. FIG. 19 shows that nanofiltration membranes coated with colloidal PEGDA-NR3 and PEGDA-NR3/NR4 maintained 80-99% less viable bacteria than an uncoated membrane even after multiple uses. FIG. 20 shows that although PEGDA-NR4 has significantly lower bactericidal activity, it prevented the adhesion of the bacteria on the membrane surface. The colloidal PEGDA-NR3/NR4 afforded a two-level antimicrobial activity through "contact-killing" and "anti-adhesion". FIG. 21 plots that water flux and dye rejection for the uncoated nanofiltration membrane and nanofiltration membrane coated with colloidal PEGDA-NR3/NR4. The water flux as shown in FIG. 21(a) was improved over the uncoated membrane due to increased surface hydrophilicity from NR4 without affecting the separation properties of the membrane as shown by the dye rejection experiment in FIG. 21(b). Deliberate fouling of the membranes showed that the nanofiltration membrane coated with colloidal PEGDA-NR3/NR4 antimicrobial and antibiofouling coating was more resistant to biofouling. FIG. 22 plots the water flux and bacterial filtration by an uncoated microfiltration membrane and coated microfiltration membrane (Example 29). It can be seen from the study that the coating did not alter the filtration properties of the membrane. Similarly, the microfiltration membrane coated with colloidal PEGDA-NR3/NR4 antimicrobial and antibiofouling coating was more resistant to biofouling. Accordingly, the instant coatings incorporate these and similar antimicrobial, anti-adhesion and anti-biofouling molecules and moieties into active polymers such as PEI, PHMB, PDDA, PQAC and similar antimicrobial polymers to construct colloidal multilevel antimicrobial and anti-biofouling coatings for surfaces.

Figure 23:
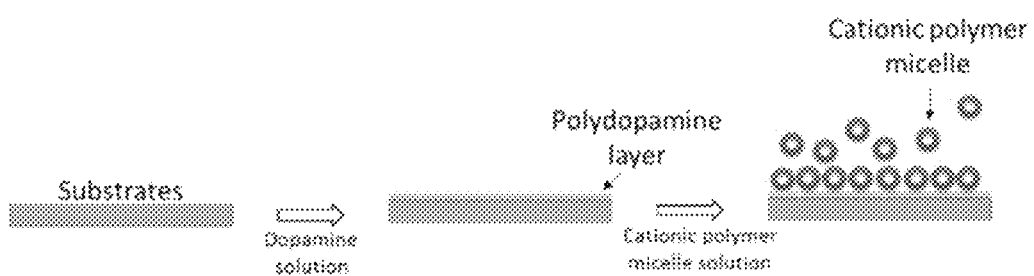
FIG. 23: Schematic drawing of the coating process for dopamine and colloidal antimicrobial and anti-biofouling coating on surfaces.
Figure 24:
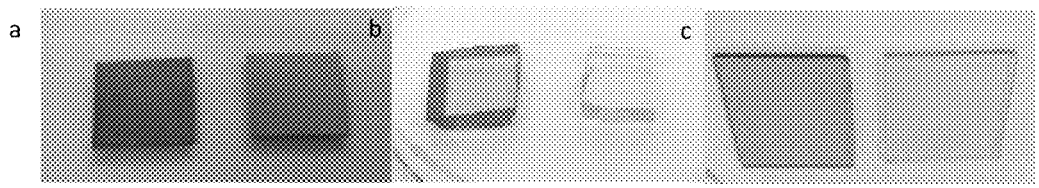
FIG. 24: Photographs of substrates coated using dopamine adhesion layer including (a) stainless steel, (b) plastic (PVC) and (c) glass.

The use of dopamine and similar materials as adhesion layer for the instant coating on surfaces is described in Example 30 and shown in the illustration of FIG. 23. The dopamine adhesion layer binds with the colloidal coating via a Schiff based reaction between catechol groups and the amine or thiol groups of the polymers. Other molecular linkers, such as vinyl sulfone, can be attached the colloidal antimicrobial and anti-biofouling coating to the subject via "click chemistry". FIG. 24 shows the colloidal antimicrobial and anti-biofouling coating on substrates with dopamine adhesion layers including stainless steel, plastic PVC and glass (Example 31). X-ray photoelectron spectroscopy of the stainless steel and plastic PVC samples in Table 4 shows that coating was successfully attached to the surfaces by the increased nitrogen content from the colloidal PEI-PHMB. Specifically, Table 4(a) shows elemental analysis results by X-ray photoelectron spectroscopy of colloidal coating on stainless steel with dopamine adhesion layer after washing in water; and Table 4(b) shows elemental analysis results by X-ray photoelectron spectroscopy of colloidal coating on plastic PVC with dopamine adhesion layer after washing in water.

TABLE 4a

| Element | Stainless steel (atomic %) | Coated stainless steel before immersion (atomic %) | Coated stainless steel after immersing three days in DDI (atomic %) | Coated stainless steel after immersing seven days in DDI (atomic %) |
|---|---|---|---|---|
| Oxygen (1s) | 18 | 19 | 23 | 14 |
| Nitrogen (1s) | 2 | 8 | 6 | 13 |
| Carbon (1s) | 74 | 71 | 64 | 69 |
| Chlorine (2p) | 0 | 0.7 | 3 | 1 |

TABLE 4b

| Element | PVC (atomic %) | Coated PVC before immersion (atomic %) | Coated PVC after immersing three days in DDI (atomic %) | Coated PVC after immersing seven days in DDI (atomic %) |
|---|---|---|---|---|
| Oxygen (1s) | 10 | 8 | 27 | 22 |
| Nitrogen (1s) | 0.6 | 5 | 6 | 5 |
| Carbon (1s) | 83 | 75 | 59 | 71 |
| Chlorine (2p) | 6 | 10 | 2 | 2 |

There was no measurable decrease in nitrogen content on the surface after 7 days of water immersion during which the substrates were placed in distilled and deionized (DDI) water at 35° C. under rapid agitations to simulate flow environment. The results indicated that the coating is compatible for use in aquatic environment and is resistant to water corrosion and erosion.

Figure 25:
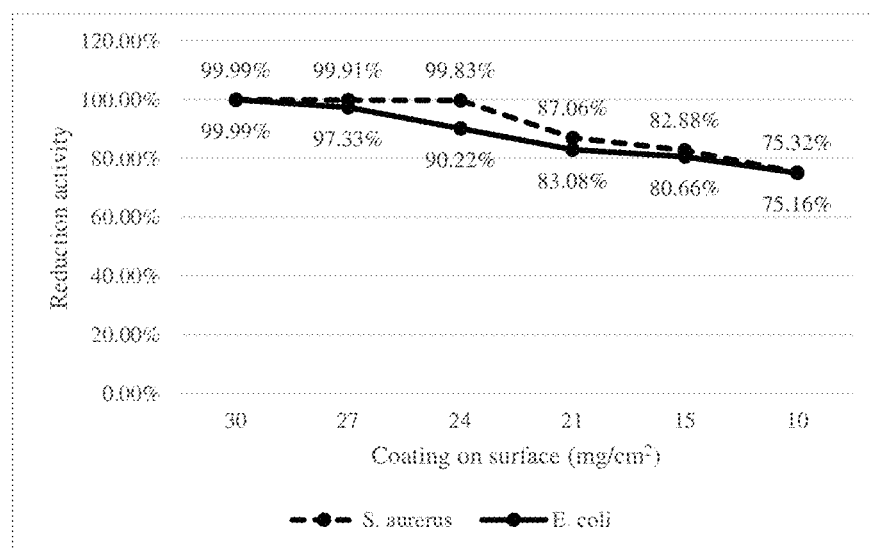
FIG. 25: Percentage reduction in viable S. aureus and E. coli bacteria on different amounts of colloidal PEI-PHMB coating (Example 8) prepared on substrate with dopamine adhesion layer.
Figure 26:
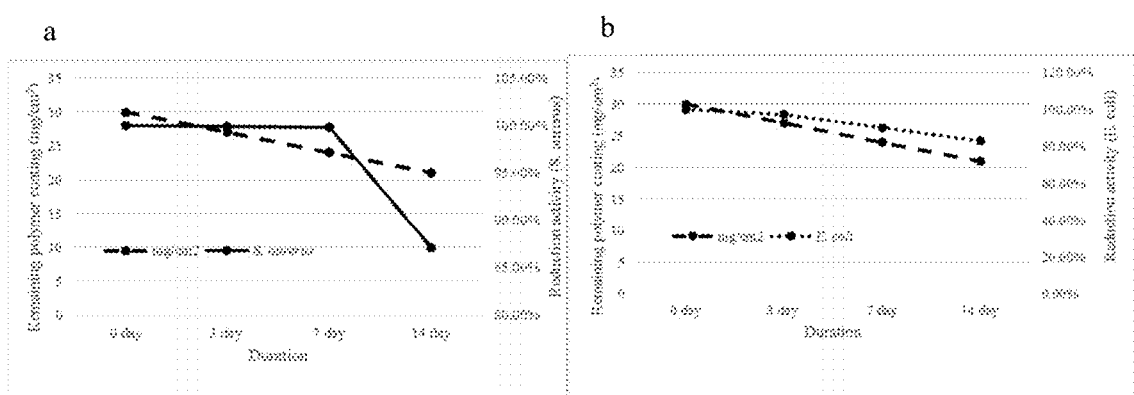
FIG. 26: Effects of accelerated ageing on the coating and bactericidal activity of colloidal PEI-PHMB coating (Example 8) for (a) S. aureus and (b) E. coli.

FIG. 25 plots the bactericidal properties of colloidal antimicrobial and anti-biofouling coating (Example 8) on substrate with dopamine adhesion layer. The plot shows the effects of the amount of coating per unit area on the bactericidal properties of the surface against Gram positive and Gram negative bacteria. The coating can attain better than 90% reduction of viable bacteria at coating level of 24 mg/cm$^2$ (wet basis) or 0.2 mg/cm$^2$ PEI and 0.05 mg/cm$^2$ PHMB (dry basis). A 99.99% (4 Log) reduction of viable bacteria can be obtained at 30 mg/cm$^2$ (wet basis) or 0.24 mg/cm$^2$ PEI and 0.06 mg/cm$^2$ PHMB (dry basis). FIGS. 26(a) and 26(b) plot the results of accelerated ageing on the coating and the resultant effects of the bactericidal properties on S. aureus and E. coli, respectively. Each experimental day was equivalent to 25 days immersion in water. The results show that the bactericidal activity can be maintained for a prolonged period of time, such as 3-14 days, more than 7 days and/or 7-14 days.

Figure 27:
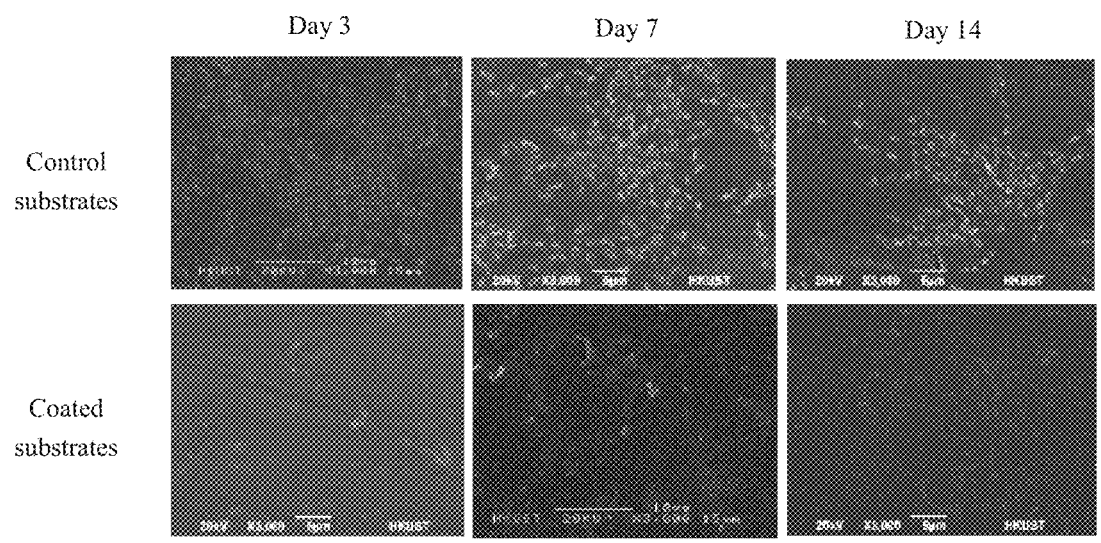
FIG. 27: SEM images of E. coli bacteria attached on uncoated stainless steel and stainless steel coated with colloidal PEI-PHMB coating (Example 8) on a dopamine adhesion layer after exposure to $10^8$ CFU/ml E. coli culture.
Figure 28:
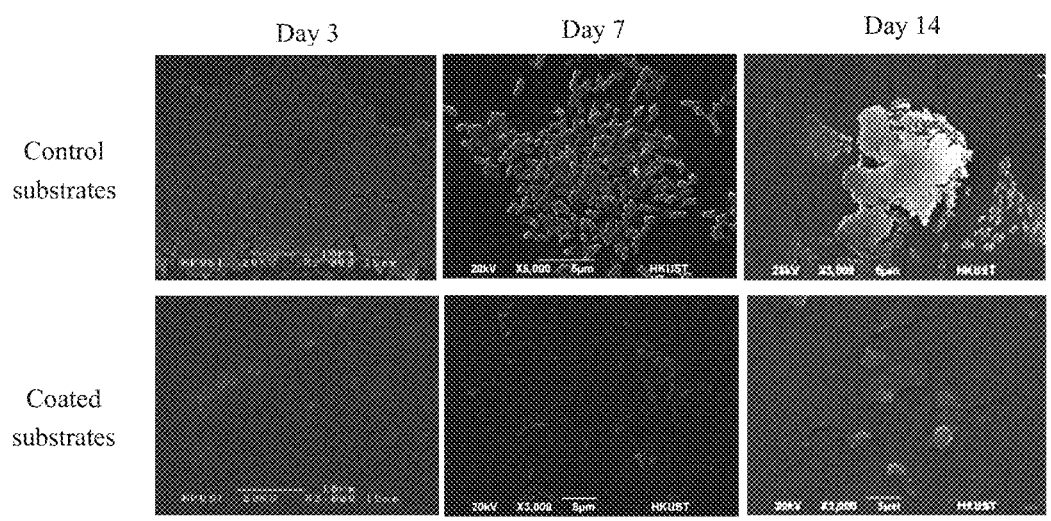
FIG. 28: SEM images of E. coli bacteria attached on uncoated plastic PVC and plastic PVC coated with colloidal PEI-PHMB coating (Example 8) on a dopamine adhesion layer after exposure to $10^8$ CFU/ml E. coli culture.
Figure 29:
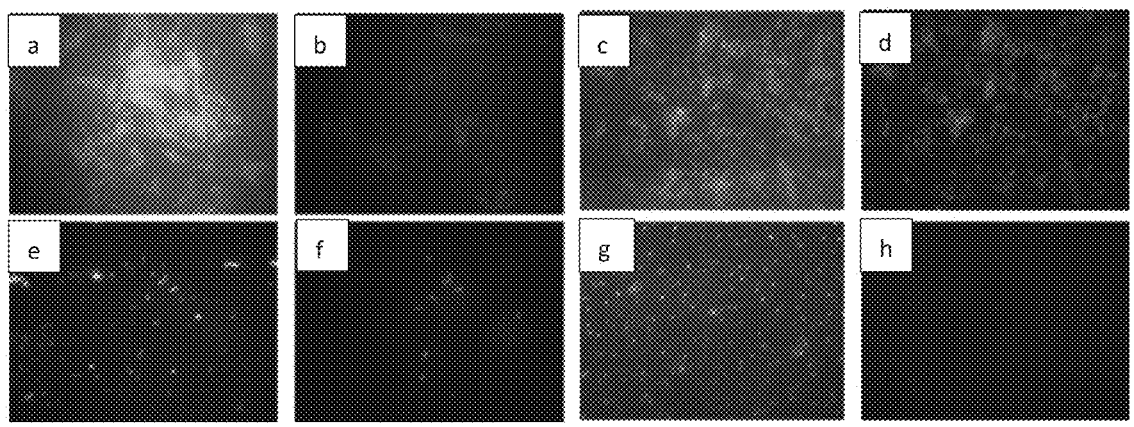
FIG. 29: Fluorescence microscopy images showing the degree of biofouling on uncoated stainless steel and stainless steel coated with colloidal PEI-PHMB coating (Example 8) on a dopamine adhesion layer after exposure to $10^8$ CFU/ml E. coli culture.
Figure 30:
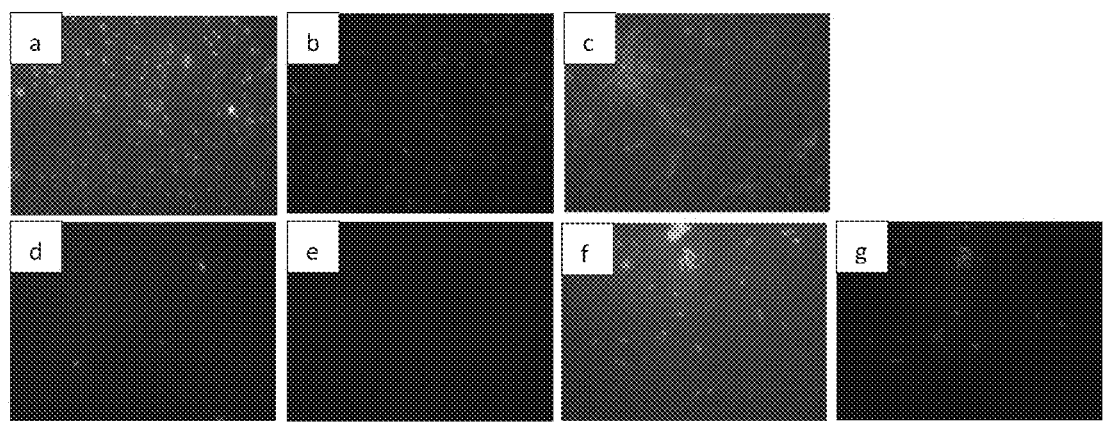
FIG. 30: Fluorescence microscopy images showing the degree of biofouling on uncoated plastic PVC and plastic PVC coated with colloidal PEI-PHMB coating (Example 7) on a dopamine adhesion layer after exposure to $10^8$ CFU/ml E. coli culture.
Figure 31:
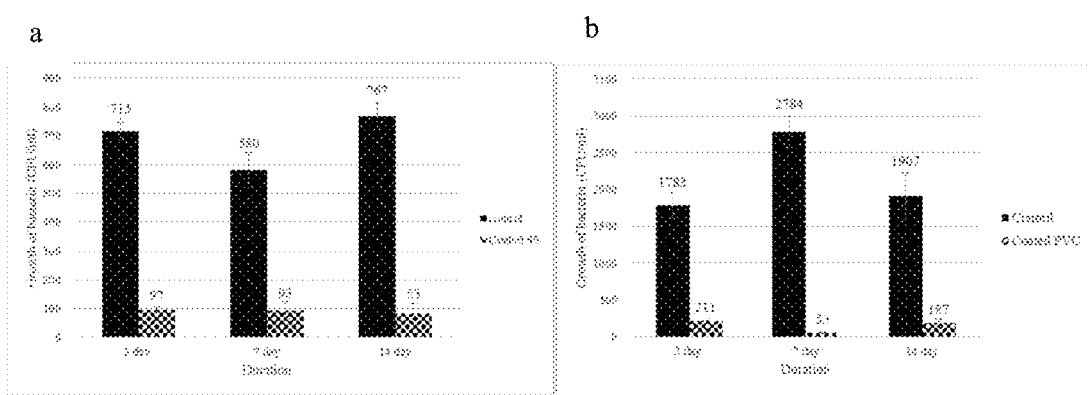
FIG. 31: Recoverable viable bacteria from uncoated and coated (a) stainless steel and (b) plastic PVC after 14 days exposure to $10^8$ CFU/ml E. coli culture.

The anti-biofouling properties of colloidal antimicrobial and anti-biofouling coating (Example 8) attached to dopamine adhesion layers on stainless steel and plastic PVC surfaces were evaluated by scanning electron microscopy in FIGS. 27 and 28, fluorescence microscopy in FIGS. 29 and 30 and direct enumeration of viable bacteria by standard microbiology method in FIG. 31. The coated and uncoated samples were immersed in 10$^8$ CFU/ml E. coli culture for 14 days. The results consistently show that there are less bacteria attachments on coated stainless steel and plastic PVC surfaces compared to the uncoated substrate as shown in FIGS. 27 and 28, and these bacteria display a difference in gross morphology compared to healthy E. coli. FIGS. 29 and 30 show significant colonization by microbial biofilm on uncoated surfaces of stainless steel and plastic PVC. The biofilms contained an organic matrix of both dead and viable bacteria cells. The coated surfaces displayed mainly fluorescence from the coating materials even after 14 days in bacteria culture. Viable bacteria were recovered from the surfaces, cultured and enumerated. The results shown in FIG. 31 indicate 90% less bacteria from coated stainless steel and plastic PVC compared to the uncoated samples. These results confirmed the long-term antimicrobial and anti-biofouling properties of the in coating in a water environment.

Figure 32:
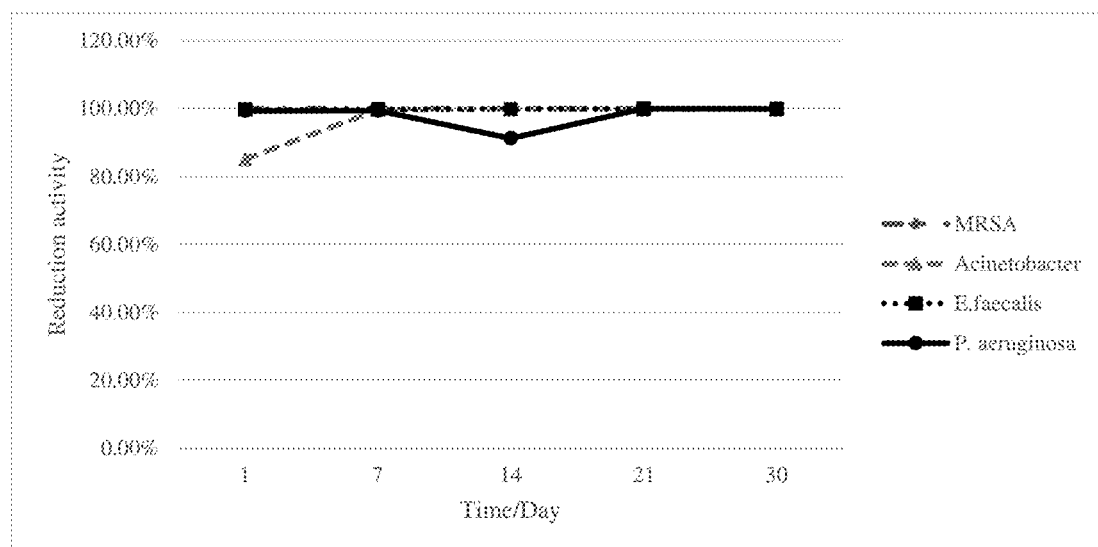
FIG. 32: Long-term bactericidal activities of hospital textile fabric coated with colloidal antimicrobial and anti-biofouling coating (Example 8) for $10^5$ CFU/ml MRSA, *E. faecalis, Acinetobacter* and *P. aeruginosa* under accelerated ageing conditions.

The colloidal antimicrobial and anti-biofouling coating was applied to porous media including textiles and nonwoven fabrics. FIG. 32 shows the performance of the coated fabric against common environmental pathogens found in hospital environment under accelerated ageing. The ageing was carried out by exposing the fabric to high temperature (50° C.) for a given duration followed by direct challenge with 10$^5$ CFU/ml bacterial solution for 1 min contact time. The results show that the coated fabric retained high bactericidal activity after 30 days of accelerated ageing study. FIG. 33(a) shows the fabrics coated with low concentration of colloidal antimicrobial and anti-biofouling coating compared well to fabric treated with alcohol and bleach solution. The fabric can attain more than a 98% reduction in viable bacteria in 1 min contact time. FIG. 33(b) shows the fabric remained bactericidal following exposure to water under rapid agitation. Compared to fabric treated with ethanol, it maintained a better than 90% bacterial reduction.

Figure 34:
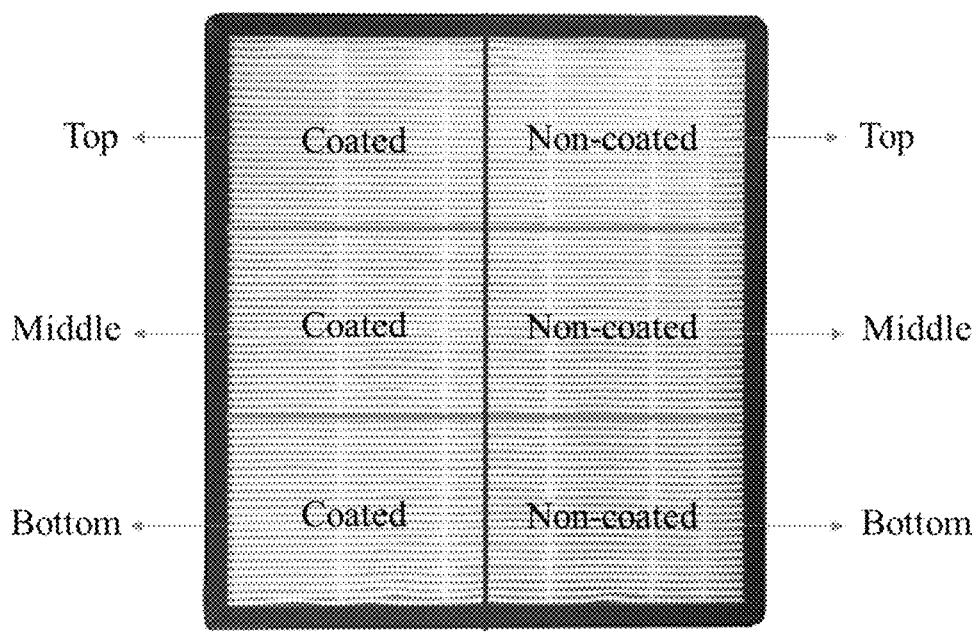
FIG. 34: A photograph of a HEPA filter spray-coated with colloidal PEI-PHMB coating and a summary of the performance against natural airborne bacteria in hospital environment.

FIG. 34 shows a HEPA filter used in the air filtration study with half of the filter coated with the colloidal antimicrobial and anti-biofouling coating and the other half uncoated. Table 5(a) shows that the micellar coating on air filter can reduce more than 78% of bacteria via contact killing over a period of 14 days.

TABLE 5a

| Duration | Total reduction |
| --- | --- |
| 2 weeks operation | 78.79% |
| 4 weeks operation | 58.75% |

The antimicrobial performance reduces to 58.75% over a period of 30 days, which may result from covered coating layer by dirt. FIG. 34 and Table 5(b) also reports that the HEPA filter coated with thyme oil encapsulated by PEI-PHMB can reduce more than 96% of bacteria via contact killing and release killing over a period of 14 days.

TABLE 5b

|  | Control | Treated samples | Bactericidal efficiency |
| --- | --- | --- | --- |
| Top | 46 | 0 | 100% |
| Center | 56 | 0 | 100% |
| Bottom | 52 | 2 | 96.15% |
| Overall reduction |  | 98.70% |  |

Compared to non-coated air filter sections, the coating layer can render bacteria nonviable when contacted with the coated surface.

The preparation of the epoxy-polymer coating materials was made on the basis of a normal anti-corrosion paint described in patent CN 1605607. It complies with the relevant specification listed in Distribution equipment and protective materials for domestic and drinking water safety evaluation standard (2011) and can be used for ship water containers, water distribution pipes, and food contacting containers. Table 6 shows the basic formula of an epoxy coating material:

TABLE 6

| Composition | Function | Weight Portion |
| --- | --- | --- |
| Epoxy resin (E-44, E-20 or E-22) | Basic material | 100 |
| Polyamide | Curing agent | 30-70 |
| Alcohol solvent (ethanol, isopropanol or butanol) | Solvent | 20-60 |
| Water | Thickener | 1-10 |

Figure 35:
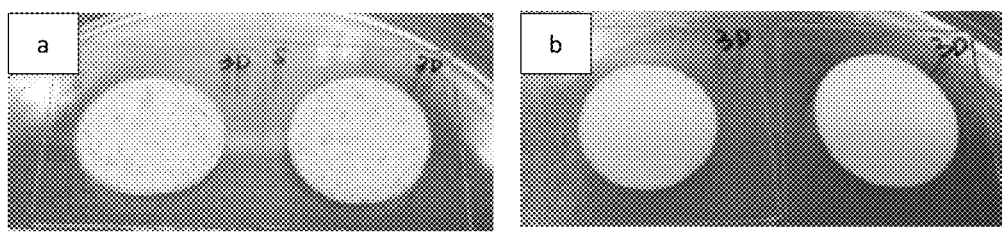
FIG. 35: Photographs of stainless steel coated with epoxy-based formulations for colloidal antimicrobial and anti-biofouling (a) coating-1 (Example 35) and (b) coating-2 (Example 36).
Figure 36:
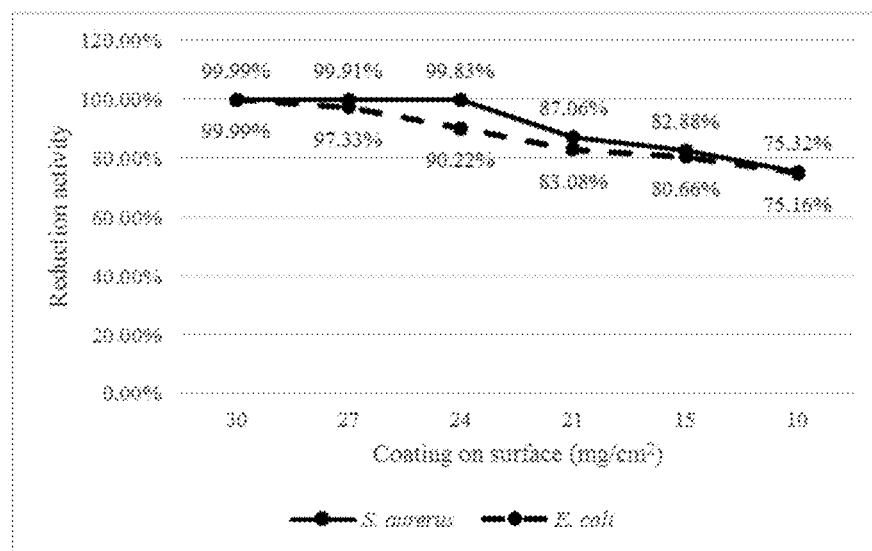
FIG. 36: Percentage reduction in viable *S. aureus* and *E. coli* bacteria on different amounts of epoxy coating-1 (Example 35) prepared on substrates.
Figure 37:
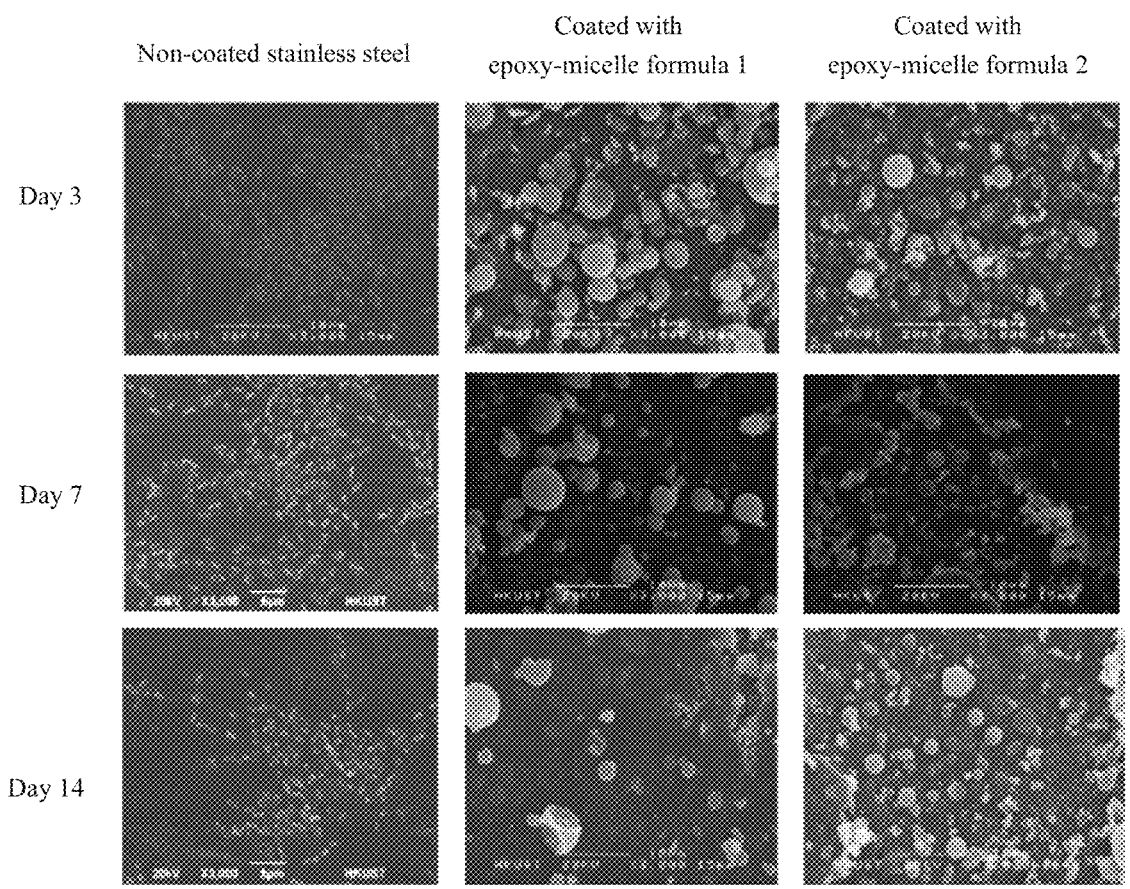
FIG. 37: SEM images of *E. coli* bacteria attached on uncoated stainless steel and stainless steel coated with epoxy coating-1 (Example 35) and coating-2 (Example 36) after exposure to $10^8$ CFU/ml *E. coli* culture.

The amount of polymer coating on the stainless steel substrates is 33 mg/cm$^2$ (FIG. 35). FIG. 36 shows the effect of the coating amount applied on the bactericidal properties of the coating. The bactericidal performance can achieve greater than 80% when the coating is over 21 mg/cm$^2$. FIG. 37 shows the adhesion of bacteria on uncoated stainless steel compared to the absence of bacteria on stainless steel coated with epoxy coating-1 (Example 35) and coating-2 (Example 36).

Figure 33:
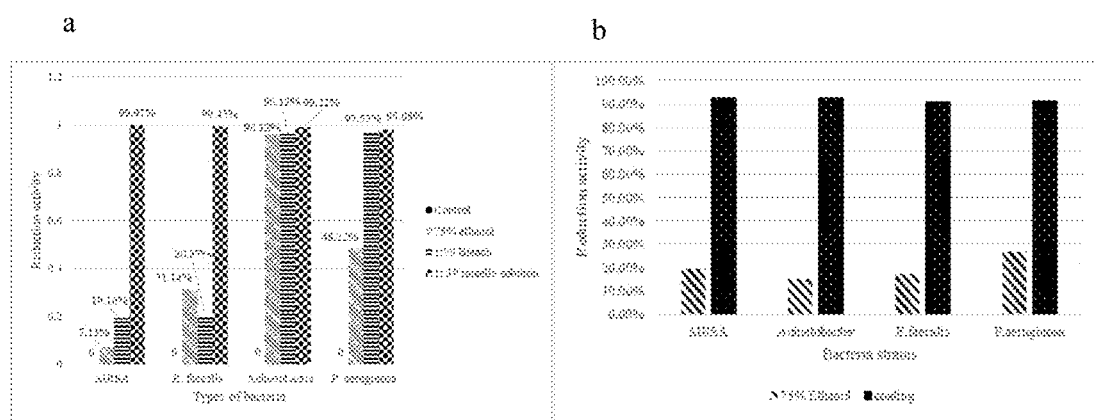
FIG. 33: (a) Bactericidal properties of uncoated, alcohol treated, bleach treated and coated (Example 12) hospital textile fabric after immersion and rapid agitation in DDI water, and (b) the bactericidal properties of alcohol treated and coated (Example 8) hospital fabric after immersion and rapid agitation in DDI water for $10^5$ CFU/ml MRSA, *E. faecalis, Acinetobacter* and *P. aeruginosa* under accelerated ageing conditions.

FIG. 33 confirmed both coatings can attain 99.9% reduction of bacterial attachment over a period of 14 days. An accelerated ageing study carried out after immersion of the coated stainless steel in water showed that the coating eroded slowly and that bactericidal activity can be maintained for a prolonged period of time.

EXAMPLES

Section 1: Colloidal Coating Formulations

Example 1. Polyethylenimine (PEI)

Polyethylenimine (PEI) with molecular weight of 1000 to 60000 g/mol was used to prepare a colloidal antimicrobial and anti-biofouling coating. Briefly, the polymer was dissolved in distilled water to prepare a PEI solution with concentration of 0.1 wt % to 40 wt %. The PEI solution was then added to a polyvinyl alcohol (PVA) solution containing 0.1 wt % to 10 wt % polymer in volume ratios from 5:1 to 1:5. Drop-by-drop addition under rapid stirring followed by ultrasonic treatment for 1 min produces the colloidal materials shown in FIG. 1.

Example 2. Functionalized Chitosan

The biopolymer chitosan and functionalized chitosan of molecular weight 5000 to 120000 g/mol were used to prepare a colloidal antimicrobial and anti-biofouling coating. Briefly, the polymer was dissolved in distilled water to prepare a biopolymer solution with concentration of 0.1 wt % to 40 wt %. The biopolymer solution was then added to a polyvinyl alcohol (PVA) solution containing 0.1 wt % to 10 wt % polymer in volume ratios from 5:1 to 1:5. Drop-by-drop addition under rapid stirring followed by ultrasonic treatment for 1 min produces the colloidal material.

Example 3. Polyquaternium

Polyquaterniums including hydroxyethylcellulose ethoxylate, poly[(2-ethyldimethyl-ammonioethyl methacrylate ethyl sulfate)-co-(1-vinylpyrrolidone)], and poly[(3-methyl-1-vinylimidazolium chloride)-co-(1-vinylpyrrolidone)] of molecular weights ranging from 5000 to 1000000 g/mol were used to prepare a colloidal antimicrobial and anti-biofouling coating. Briefly, the polymer was dissolved in distilled water to prepare the polyquaternium solution with concentration of 0.1 wt % to 40 wt %. The polyquaternium solution was then added to a polyvinyl alcohol (PVA) solution containing 0.1 wt % to 10 wt % polymer in volume ratios from 5:1 to 1:5. Drop-by-drop addition under rapid stirring followed by ultrasonic treatment for 1 min produces the colloidal material.

Example 4. Polymeric Cross-Linking

The shape and size of the colloid was adjusted by cross-linking the active polymers (FIG. 2) with a third polymer such as poly(ethylene glycol) methacrylate or Poly(ethylene glycol) methyl ether methacrylate of molecular weight 500 to 950 g/mol for PEI-based colloidal antimicrobial and anti-biofouling coating.

Example 5. PEI+PDDA (Ratio 1:1)

The polyethylenimine (PEI) with molecular weight of 1000 to 60000 g/mol was dissolved in distilled water to prepare a PEI solution with concentrations of 10 wt % to 20 wt %. The poly(diallyldimethylammonium chloride) (PDDA) with molecular weight of 150000-230000 g/mol was dissolved in water to prepare a PDDA solution with concentrations of 10 wt % to 20 wt %. Equal volumes of PEI and PDDA solutions of same concentrations were rapidly mixed together followed by 1 min ultrasonication to produce a colloidal PEI:PDDA of 1:1 ratio.

Example 6. PHMB+PDDA (Ratio 1:1)

The polyhexamethylene biguanide (PHMB) with molecular weight of 2000-2600 g/mol was dissolved in distilled water to prepare a PHMB solution with concentrations of 10 wt % to 20 wt %. The poly(diallyldimethylammonium chloride) (PDDA) with molecular weight of 150000-230000 g/mol was dissolved in water to prepare a PDDA solution with concentrations of 10 wt % to 20 wt %. Equal volumes of PHMB and PDDA solutions of same concentrations were rapidly mixed together followed by 1 min ultrasonication to produce a colloidal PHMB:PDDA of 1:1 ratio.

Example 7. PEI+PHMB (Ratio 1:1)

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 10 wt % to 20 wt %. Equal volumes of PEI and PHMB solutions of same concentrations were rapidly mixed together followed by 1 min ultrasonication to produce a colloidal PEI:PHMB of 1:1 ratio. The colloid was diluted to obtain a final PEI (1-6 wt %) and PHMB (1-6 wt %) concentrations of 2-12 wt %.

Example 8. PEI+PHMB (Ratio 4:1)

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 2.5 wt % to 5 wt %. Equal volumes of PEI and PHMB solutions were rapidly mixed together followed by 1 min ultrasonication to produce a colloidal PEI:PHMB of 4:1 ratio as shown in FIG. 3a. The colloid was diluted to obtain a final PEI of 1-6 wt % and PHMB of 0.25-1.5 wt %.

Example 9. PEI+PHMB (Ratio 2:1)

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 5 wt % to 10 wt %. Equal volumes of PEI and PHMB solutions were rapidly mixed together followed by 1 min ultrasonication to produce a colloidal PEI:PHMB of 2:1 ratio as shown in FIG. 3b. The colloid was diluted to obtain a final PEI of 1-6 wt % and PHMB of 0.5-3 wt %.

Example 10. PEI+PHMB (Ratio 1:2)

The polyethylenimine (PEI) with molecular weight of 10000 g/mol was dissolved in distilled water to prepare a PEI solution with concentrations of 5 wt % to 10 wt %. The polyhexamethylene biguanide (PHMB) with molecular of 2000-2600 g/mol was dissolved in distilled water to prepare a PHMB solution with concentrations of 10 wt % to 20 wt %. Equal volumes of PEI and PHMB solutions were rapidly mixed together followed by 1 min ultrasonication to produce a colloidal PEI:PHMB of 1:2 ratio as shown in FIG. 3c. The colloid was diluted to obtain a final PEI of 0.5-3 wt % and PHMB of 1-6 wt %.

Example 11. PEI+PHMB (Ratio 1:4)

The polyethylenimine (PEI) with molecular weight of 10000 g/mol was dissolved in distilled water to prepare a PEI solution with concentrations of 5 wt % to 10 wt %. The polyhexamethylene biguanide (PHMB) with molecular of 2000-2600 g/mol was dissolved in distilled water to prepare a PHMB solution with concentrations of 10 wt % to 20 wt %. Equal volumes of PEI and PHMB solutions were rapidly mixed together followed by 1 min ultrasonication to produce a colloidal PEI:PHMB of 1:2 ratio as shown in FIG. 3d. The colloid was diluted to obtain a final PEI of 0.25-1.5 wt % and PHMB of 1-6 wt %.

Example 12. PEI+PHMB (Ratio 39:1)

The polyethylenimine (PEI) with molecular weight of 1200 to 10000 g/mol was dissolved in distilled water to prepare a PEI solution with concentrations of 5 wt % to 10 wt %. The polyhexamethylene biguanide (PHMB) with molecular of 2000-2600 g/mol was dissolved in distilled water to prepare a PHMB solution with concentrations of 10 wt % to 20 wt %. Equal volumes of PEI and PHMB solutions were rapidly mixed together followed by 1 min ultrasonication to produce a colloidal PEI:PHMB of 39:1 ratio. The colloid was diluted to obtain a final PEI of 1-6 wt % and PHMB of 0.025%-0.15%.

Example 13. PHMB+Thyme Oil (1:5)

The polyhexamethylene biguanide (PHMB) with molecular weight of 2000-2600 g/mol was dissolved in distilled water to prepare a PHMB solution with concentrations of 5 wt % to 20 wt %. A measured amount of thyme oil was added to 0.1 to 10 wt % PVA solution and emulsified. Equal volumes of PHMB and thyme oil/PVA solutions were rapidly mixed together followed by 1 min ultrasonication to produce PHMB-encapsulated thyme oil. Tween 80 was added to stabilize the resulting colloid as shown in FIG. 4a.

Example 14. PEI+Thyme Oil (1:5)

The polyethylenimine (PEI) with molecular weight of 1200 to 10000 g/mol was dissolved in distilled water to prepare a PEI solution with concentrations of 5 wt % to 10 wt %. A measured amount of thyme oil was added to 0.1 to 10 wt % PVA solution and emulsified. Equal volumes of PEI and thyme oil/PVA solutions were rapidly mixed together followed by 1 min ultrasonication to produce PEI-encapsulated thyme oil. Tween 80 was added to stabilize the resulting colloid as shown in FIG. 4b.

Example 15. PEI+PHMB+Thyme Oil

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 10 wt % to 20 wt %. A measured amount of thyme oil was added to 0.1 to 10 wt % PVA solution and emulsified. A given amount of PEI solution was added followed by 1 min ultrasonication, and the appropriate volume of PHMB solution was then added followed by another 1 min ultrasonication to produce colloidal PEI:PHMB:thyme oil materials shown in FIG. 5. Tween 80 was added to stabilize the resulting colloid.

Example 16. PEI+Cinnamaldehyde

The polyethylenimine (PEI) with molecular weight of 1200 to 10000 g/mol was dissolved in distilled water to prepare a PEI solution with concentrations of 5 wt % to 10 wt %. A measured amount of cinnamaldehyde was added to 0.1 to 10 wt % PVA solution and emulsified. Equal volumes of PEI and cinnamaldehyde/PVA solutions were rapidly mixed together followed by 1 min ultrasonication to produce PEI-encapsulated cinnamaldehyde. Tween 80 was added to stabilize the resulting colloid as shown in FIG. 6a.

Example 17. PHMB+Cinnamaldehyde

The polyhexamethylene biguanide (PHMB) with molecular weight of 2000-2600 g/mol was dissolved in distilled water to prepare a PHMB solution with concentrations of 5 wt % to 20 wt %. A measured amount of cinnamaldehyde was added to 0.1 to 10 wt % PVA solution and emulsified. Equal volumes of PHMB and cinnamaldehyde/PVA solutions were rapidly mixed together followed by 1 min ultrasonication to produce PHMB-encapsulated cinnamaldehyde. Tween 80 was added to stabilize the resulting colloid.

Example 18. PEI+PHMB+Cinnamaldehyde

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mole was dissolved in distilled water to prepare a PHMB solution with concentrations of 10 wt % to 20 wt %. A measured amount of cinnamaldehyde was added to 0.1 to 10 wt % PVA solution and emulsified. A given amount of PEI solution was added followed by 1 min ultrasonication, and the appropriate volume of PHMB solution was then added followed by another 1 min ultrasonication to produce colloidal PEI:PHMB:cinnamaldehyde materials. Tween 80 was added to stabilize the resulting colloid.

Example 19. PEI+Farnesol

The polyethylenimine (PEI) with molecular weight of 1200 to 10000 g/mol was dissolved in distilled water to prepare a PEI solution with concentrations of 5 wt % to 10 wt %. A measured amount of farnesol dissolved in DMSO/water solution to obtain 10 wt % to 50 wt %. The farnesol solution was added to 0.1 to 10 wt % PVA solution and emulsified. Equal volumes of PEI and farnesol/PVA solutions were rapidly mixed together followed by 1 min ultrasonication to produce PEI-encapsulated farnesol. Tween 80 was added to stabilize the resulting colloid as shown in FIG. 6b.

Example 20. PHMB+Farnesol

The polyhexamethylene biguanide (PHMB) with molecular weight of 2000-2600 g/mol was dissolved in distilled water to prepare a PHMB solution with concentrations of 5 wt % to 20 wt %. A measured amount of farnesol dissolved in DMSO/water solution to obtain 10 wt % to 50 wt %. The farnesol solution was added to 0.1 to 10 wt % PVA solution and emulsified. Equal volumes of PHMB and farnesol/PVA solutions were rapidly mixed together followed by 1 min ultrasonication to produce PHMB-encapsulated farnesol. Tween 80 was added to stabilize the resulting colloid.

Example 21. PEI+PHMB+Farnesol

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 10 wt % to 20 wt %. A measured amount of farnesol dissolved in DMSO/water solution to obtain 10 wt % to 50 wt %. The farnesol solution was added to 0.1 to 10 wt % PVA solution and emulsified. A given amount of PEI solution was added followed by 1 min ultrasonication, and the appropriate volume of PHMB solution was then added followed by another 1 min ultrasonication to produce colloidal PEI:PHMB:farnesol materials. Tween 80 was added to stabilize the resulting colloid.

Example 22. PEI+PHMB+Mixed Biocides

The polyethylenimine (PEI) with molecular weight of 10000 g/mol was dissolved in distilled water to prepare a PEI solution with concentrations of 10 wt % to 20 wt %. The polyhexamethylene biguanide (PHMB) with molecular of 2000-2600 g/mol was dissolved in distilled water to prepare a PHMB solution with concentrations of 10 wt % to 20 wt %. A mixed biocide containing thyme oil, cinnamaldheyde and farnesol was prepared. The mixed biocides solution was added to 0.1 to 10 wt % PVA solution and emulsified. A given amount of PEI solution was added followed by 1 min ultrasonication, and the appropriate volume of PHMB solution was then added followed by another 1 min ultrasonication to produce colloidal PEI:PHMB:mixed biocides shown in FIG. 6c. Tween 80 was added to stabilize the resulting colloid.

Section 2: Select Applications

Example 23. Anti-Biofouling Coating for Water Filtration Membranes

The colloidal antimicrobial and anti-biofouling coating was coated on water filtration membranes by filtration. The process was carried out under 0.01 MPa transmembrane-pressure and the coating can be adjusted from 0.1 to 10 wt %. Coating can also be carried out via spray coating, wash-coating and dip-coating methods.

Example 24. Anti-Biofouling Coating for Reverse Osmosis (RO) Membranes

The colloidal antimicrobial and anti-biofouling coating was coated on RO membranes by dead-end filtration. The process was carried out under 0.1 MPa transmembrane pressure and the coating can be adjusted from 0.1 to 10 wt %. Coating can also be carried out via spray coating, wash-coating and dip-coating methods.

Example 25. Anti-Biofouling Coating for Nanofiltration (NF) Membranes

The colloidal antimicrobial and anti-biofouling coating was coated on nanofiltration membranes by dead-end filtration. The process was carried out under 0.1 MPa transmembranepressure and the coating can be adjusted from 0.1 to 10 wt %. Coating can also be carried out via spray coating, wash-coating and dip-coating methods.

Example 26. Anti-Biofouling Coating for Ultrafiltration (UF) Membranes

The colloidal antimicrobial and anti-biofouling coating was coated on ultrafiltration membranes by dead-end filtration. The process was carried out under 0.05 MPa transmembrane pressure and the coating can be adjusted from 0.1 to 10 wt %. Coating can also be carried out via spray coating, wash-coating and dip-coating methods.

Example 27. Anti-Biofouling Coating for Microfiltration (MF) Membranes

The colloidal antimicrobial and anti-biofouling coating was coated on microfiltration membranes by dead-end filtration. The process was carried out under 0.05 MPa transmembrane pressure and the coating can be adjusted from 0.1 to 10 wt %. Coating can also be carried out via spray coating, wash-coating and dip-coating methods.

Example 28. Anti-Biofouling Coating (Crosslinked Molecular Moieties) for NF Membranes A colloidal antimicrobial and anti-biofouling coating prepared from cross-linking PEGDA polymer with L-α-phosphatidylcholine (EGG), 2-(diethylamino)ethylmethacrylate (NR3), [3-(methacryloylamino)propyl]dimethyl(3-sulfopropyl)ammonium hydroxide (NR4), 3-sulfopropyl methacrylate (SO3) and Lysozyme (LYN). The bactericidal activities of colloidal PEGDA-EGG, PEGDA-NR3, PEGDA-NR4, PEGDA-SO3, PEGDA-LYN as well as cross-linked with unmodified chitosan, PEGDA-CHI are reported in FIG. 17. The colloidal coating was brush-coated onto nanofiltration membranes, but other coating methodologies including filtration, spray-coating, wash-coating and dip-coating techniques could also be used. The performance of PEGDA-NR3, PEGDA-NR4 and PEGDA-NR3/NR4 coated on nanofiltration membranes was plotted in FIGS. 18-20.

Example 29. Anti-Biofouling Coating (Crosslinked Molecular Moieties) for MF Membranes A colloidal antimicrobial and anti-biofouling coating prepared from cross-linking PEGDA polymer with L-α-phosphatidylcholine (EGG), 2-(diethylamino)ethylmethacrylate (NR3), [3-(methacryloylamino)propyl]dimethyl(3-sulfopropyl)ammonium hydroxide (NR4), 3-sulfopropyl methacrylate (SO3) and Lysozyme (LYN). The colloidal coating was spray-coated onto microfiltration membranes, but other coating methodologies including filtration, brush-coating, wash-coating and dip-coating techniques could also be used. The performance of PEGDA-NR3/NR4 coated on MF membranes was reported in FIG. 21

Example 30. Antimicrobial and Anti-Biofouling Coatings Using Dopamine as an Adhesion Layer The colloidal antimicrobial and anti-biofouling coating was coated on surfaces with dopamine or similar molecular adhesion layer. A 2 mg/ml dopamine solution was prepared from tris-Hcl buffer (pH 8.5) solution. The adhesion layer was coated on surface by spray-coating, brush-coating, wash-coating and dip-coating or similar methods. Excess dopamine was removed by rinsing and the sample was dried before coating with the colloidal antimicrobial and anti-biofouling coating as illustrated in FIG. 23.

Example 31. High-Resistant Coating Using Dopamine as Adhesion Layer

The colloidal antimicrobial and anti-biofouling coating was coated on surface with dopamine adhesion layer deposited on stainless steel, plastic PVC and glass (FIG. 24). The coating on the surfaces was resistant to water even under agitation as indicated in an accelerated study in FIG. 26. The antimicrobial and anti-biofouling properties were maintained even under high microbial contamination as indicated in FIGS. 26-31.

Example 32. Antimicrobial and Anti-Biofouling Coatings on Woven and Nonwoven Textiles The colloidal antimicrobial and anti-biofouling coating was diluted by 2 and 4 times and applied onto textile materials via wet coating process. The coating can also be applied by spray-coating, dip-coating, and related coating methods. Furthermore, the coating can be added during the rinse cycle in machine washing of the textile fabrics.

Example 33. High-Resistant Coating on Woven and Nonwoven Textiles

The colloidal antimicrobial and anti-biofouling coating was coated onto hospital bed partition fabrics. FIGS. 32 and 33 summarizes the bactericidal properties of the coated fabric against a range of Gram-positive and Gram-negative bacteria including pathogens and drug-resistant microorganisms. The result of accelerated ageing in FIG. 32 showed that the coated fabric remain bactericidal for long period of time. Repeated immersion in water under rapid agitation did not affect the bactericidal properties of the coated fabric (cf. FIG. 33).

Example 34. Antimicrobial Coating on Particulate Air Filters

The colloidal antimicrobial and anti-biofouling coatings given in examples 1-12 and examples 13-22 were coated on particulate air filters including HEPA by a spray-coating method. Electrospraying method, dip-coating, wash-coating and related methods could also be used as an alternative. FIG. 34 is a picture of a HEPA filter spray coated with the colloidal 1 PEI: 1 PHMB coating and its antimicrobial properties for airborne bacteria.

Example 35. Epoxy-Based Formulation for Colloidal Antimicrobial and Anti-Biofouling Coating-1

A typical formulation was prepared by mixing 100 parts by volume of epoxy resin with 30-70 parts by volume of curing agent and 100-200 parts by volume of a colloidal antimicrobial and anti-biofouling coating in example 8. A 20-60 parts by volume of solvent was added followed by rapidly mixing.

Example 36. Epoxy-Based Formulation for Colloidal Antimicrobial and Anti-Biofouling Coating-2

A typical formulation was prepared by mixing 100 parts by volume of epoxy resin with 30-70 parts by volume of curing agent and 100-200 parts by volume of a colloidal antimicrobial and anti-biofouling coating in example 11. A 20-60 parts by volume of solvent was added followed by rapidly mixing.

Example 37. Antimicrobial Epoxy Surface Coating

Figure 38:
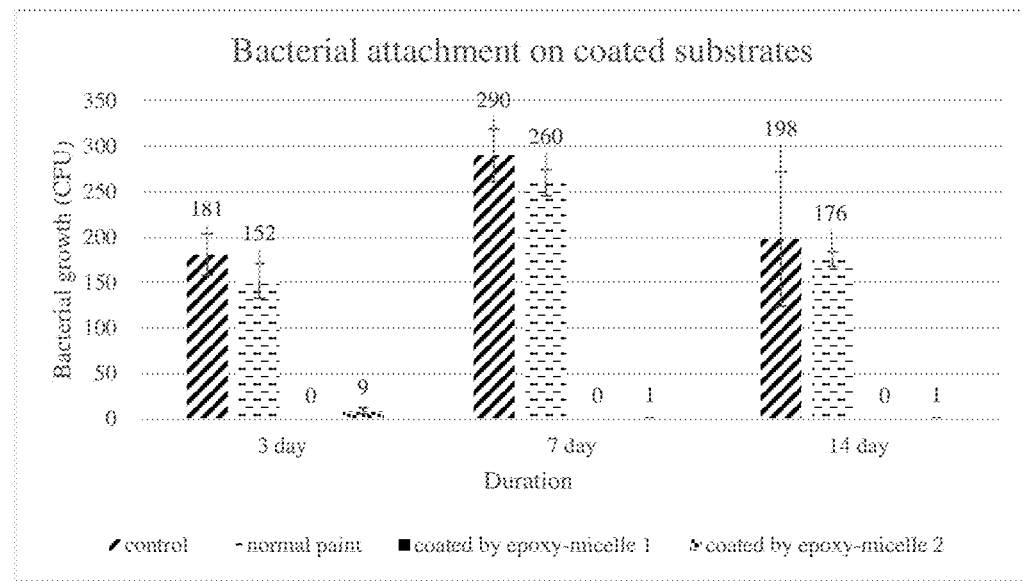
FIG. 38: Plots of *E. coli* attached to uncoated stainless steel and stainless steel coated with epoxy coating-1 (Example 35) and coating-2 (Example 36).
Figure 39:
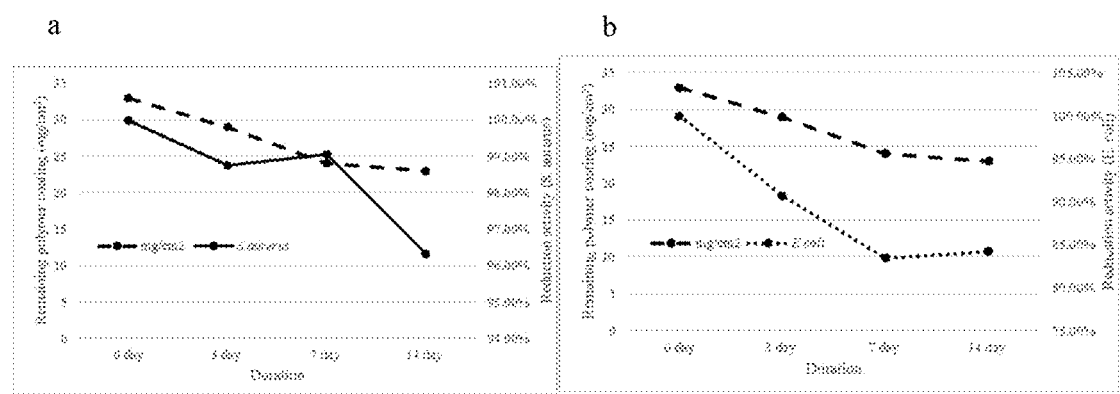
FIG. 39: Effects of accelerated ageing on the coating and bactericidal activity of epoxy coating (Example 35) for $10^6$CFU/ml (a) *S. aureus* and (b) *E. coli*.

The epoxy coatings described in examples 35 & 36 were coated onto stainless steel chucks as shown FIG. 35 and used for antimicrobial studies (FIGS. 37-39).

Section 3: Methods

Characterization

SEM images of initial membrane, membrane with antimicrobial formulation, initial substrates and substrates coated with antimicrobial formulations were made using JEOL JSM-6300 and JEM-6300F scanning electron microscopes equipped with energy dispersive X-ray detectors.

X-Ray Photoelectron Spectroscopy

Analyses of element composition on initial substrates and substrates coated with antimicrobial formulation were made using Model PHI 5600 (Physical Electronics), equipped with multi-technique system (AES, SAM, XPS).

Fluorescence Microscope

Analyses of distribution of biofouling on initial substrates and substrates coated with antimicrobial formulation were made using Nikon TE2000E-PFS. •Dual-View Micro-imager Test Studies Protocols Antimicrobial Activity Bacteria prepared from re-culture were diluted to $10^6$ CFU/mL. 100 µL of the diluent was dropped on each of the carrier. A timer was used to monitor the contact time of the carrier with bacteria. Afterwards, the carriers were transferred to a sterile bottle containing 10 mL of neutralizer solution; 0.9% (W/V) NaCl, 0.2% w/v tween 80 and 0.001 M sodium thiosulphate. It was allowed for incubation for 30 minutes.

Bacteria were serially diluted with sterilized saline solution if necessary. 100 µL of the solution was inoculated into TSA agar and cultured for 24 hours. The plates were taken out and enumerated by counting the colony forming unit (CFU).

Anti-Adhesion Tests

In the anti-adhesion test, coated and uncoated membranes were exposed to $10^8$ CFU/ml E. coli in nutrient broth under static batch conditions simulating worse possible scenario over a period of 14 days. After incubation, the membranes were gently washed with sterile DDI water to remove the suspended microbes. The washed membranes were then observed under scanning electron microscope (SEM) to search and estimate the density of adhered bacteria on the membrane surface. The SEM used was model JEOLJSM 6300F.

Membrane Permeability

Water permeation was measured with a membrane in a dead-end filtration cell. Under the pressure of 300 kPa and at the feed temperature of 25° C., the flux of deionized water was obtained from the volume of the permeated water within 60 min. The acridine orange sieving tests were conducted on the membrane using the same device. Feed solutions with concentration of 0.1 g/L were prepared. Under the pressure of 300 kPa and at the feed temperature of 25° C., permeates were collected within 30 min. The concentration of acridine orange in the feeds and permeates was measured by UV-vis. Rejection (R) before and after modification was calculated according to the equation $R=1-C_p/C_f$, where $C_p$ and $C_f$ are the UV-vis concentrations in permeate and feed, respectively.

Biofilm Staining

The stain used to dye biofilms was Filmtracer™ LIVE/DEAD® Biofilm Viability Kit. The staining protocol followed the manufacturers' instructions. Briefly, the polymer micellar solution coated stainless steel and PVC samples were put into petri dish which contained 10 ml nutrient broth with $E.\ coli$ of $10^8$ CFU/ml. After culture, PBS was used to wash the non-attached bacteria off the substrate surface and transferred the rinsed substrates into a 6-well plate. The working solution of stain was prepared by adding 3 μl of SYTO 9 and 3 μl of propidium iodide stain to 1 ml of filtered-sterilized water. Then add 200 μl stains which is mixed according to the manufacturer. The staining dish was incubated for 20-30 minutes in dark. After staining, the samples were rinsed with filtered-sterilized water for three times in order to remove all excess stain.

Stability of Micellar Solution on Membranes

Tests were carried out to investigate the stability of the treated membrane. The treated membrane was installed in the cross-flow membrane filtration cell shown in FIG. 6 and retentate flow at 3 bar was maintained. The retentate was collected and analyzed for eluted anti-biofoulant by a colorimetric method using UV-Vis spectrometer. The results showed that the membrane retained better than 85% of the filtered anti-biofoulant.

Stability of Micellar Solution on Multiple Surfaces

The coated samples were exposed to 50 ml deionized distilled water and shaken at 100-200 rpm for 14 days. The leaching polymers in the solution were measured by UV-vis spectrophotometer. The antimicrobial activity of remaining coating on the samples was tested.

What is claimed is:

1. An antimicrobial and anti-biofouling coating formulation, comprising:
    a hollow round colloidal structure, comprising:
        an active polymer shell; and
        an active or inert core,
    wherein the active polymer shell comprises polymers with antimicrobial and anti-biofouling activities, including polyethylenimine (PEI), poly(diallyldimethylammonium chloride) (PDDA) and polyhexamethylene biguanide (PHMB),
    wherein the core is active and contains one or more disinfectants, biocides and fragrances,
    wherein the core is inert and contains water or an inert solvent,
    wherein the hollow round colloidal structure is stable for at least 3 months, and
    wherein a size of the hollow round colloidal structure is between 0.5 μm and 20 μm, the size being controlled by adjusting molecular weights and compositional ratios of the polymers.

2. The coating formulation according to claim 1, wherein the polymers are present in a concentration of 0.5-100 wt % of the polymer shell.

3. The coating formulation according to claim 2, wherein the polymers are present in a concentration of 10-20 wt % of the polymer shell.

4. The coating formulation according to claim 1, wherein the core is an active core comprising one or more biocides selected from the group consisting of essential oil, polyol and aldehyde.

5. The coating formulation according to claim 4, wherein the biocide is an essential oil and the essential oil is thyme oil.

6. The coating formulation according to claim 4, wherein the biocide is a polyol and the polyol is farnesol.

7. The coating formulation according to claim 4, wherein the biocide is an aldehyde and the aldehyde is cinnamaldehyde.

8. The coating formulation according to claim 4, wherein the one or more biocides comprises an essential oil and the essential oil is thyme oil, a polyol and the polyol is farnesol and an aldehyde and the aldehyde is cinnamaldehyde.

9. The coating formulation according to claim 1, wherein the active polymer shell comprises 0.0001-5% (w/v) of the PEI, having a mw of 1,200-60,000 g/mol, 0.05-3% (w/v) of the PHMB, having a mw of 2,000-2,600 g/mol, and 0.01-20% (w/v) of the PDDA, having a mw of 250,000-350,000 g/mol, and wherein the active core contains 0.01-1.5% (w/v) of thyme oil, 0.01-1.5% (w/v) of farnesol, and 0.05-1.5% (w/v) of cinnamaldehyde.

10. The coating formulation of claim 9, wherein the coating formulation further comprises:
    0.01-20% (w/v) of polyvinyl alcohol having a mw 31,000-186,000 g/mol;
    0.01-20% (w/v) of PEGMA having a Mn of 500; and
    0.01-20% (w/v) of MPEGMA having a Mn of 950.

11. The coating formulation of claim 1, wherein the coating formulation further comprises stabilizers.

12. A method of producing antimicrobial and anti-biofouling coating for application to nonporous surfaces, porous membranes or porous materials, comprising:
    preparing an antimicrobial and anti-fouling formulation by the steps of:
        preparing an aqueous solution containing one or more active polymers, wherein the one or more active polymers are selected from the group consisting of polyquaternium, poly(diallyldimethylammonium chloride) (PDDA) and polyhexamethylene biguanide (PHMB);
        adding biocides or solvents into the aqueous solution of active polymers;
        preparing an emulsion having a hollow round colloidal structure comprising adding a stabilizer mixture containing one and more surfactants to the biocides or solvents and solution of active polymers to form the antimicrobial and anti-fouling formulation; and
        preparing the antimicrobial and anti-fouling coating from the antimicrobial and anti-fouling formulation; and
    applying the antimicrobial and anti-fouling coating on nonporous surfaces, porous membranes or porous materials.

13. The method according to claim 12, wherein the nonporous surfaces are stainless steel, glass and polyvinyl chloride surfaces.

14. The method according to claim 12, wherein the porous membranes are selected from the group consisting of reverse osmosis membranes, nanofiltration membranes, ultrafiltration membranes, microfiltration membranes and high-efficiency particulate air filters.

15. The method according to claim 12, wherein the porous materials are nonwoven and woven fabric materials.

16. The method according to claim 12, wherein the surfactants are polyvinyl alcohol and polyethylene glycol.

17. The method according to claim 12, wherein applying the antimicrobial and anti-biofouling coating comprises at least one of wiping, brushing, casting, dip-coating, wash-coating, spin-coating, spray-coating and layer-by-layer coating the antimicrobial and anti-biofouling formulation onto nonporous surfaces, porous membranes or porous materials.

18. The method according to claim 12, wherein applying the antimicrobial and anti-biofouling coating comprises incorporating the antimicrobial and anti-biofouling formulation into a paint or an epoxy resin for direct application on nonporous surfaces, porous membranes or porous materials.

19. The method according to claim 12, wherein applying the antimicrobial and anti-biofouling coating on porous membranes further comprises rejecting round colloids on the surfaces of porous membranes by a further filtration method thereby forming a reversible coating.

20. An antimicrobial and anti-biofouling coating formulation, comprising:
  a hollow round colloidal structure, comprising:
    an active polymer shell; and
    an active core, wherein the core contains one or more disinfectants, biocides and fragrances,
  wherein the active polymer shell comprises 0.0001-5% (w/v) polyethylenimine (PEI) having a mw of 1,200-60,000 g/mol, 0.05-3% (w/v) polyhexamethylene biguanide (PHMB) having a mw of 2,000-2,600 g/mol, and 0.01-20% (w/v) of poly(diallyldimethylammonium chloride) (PDDA) having a mw of 250,000-350,000 g/mol, and wherein the active core contains 0.01-1.5% (w/v) of thyme oil, 0.01-1.5% (w/v) of farnesol, 0.05-1.5% (w/v) of cinnamaldehyde,
  wherein the core is active and contains one or more disinfectants, biocides and fragrances,
  wherein the hollow round colloidal structure is stable for at least 3 months.

* * * * *